(12) United States Patent
Kim et al.

(10) Patent No.: US 8,288,443 B2
(45) Date of Patent: Oct. 16, 2012

(54) MODIFIED GLASS FIBER WITH MONOLAYER OF AMINOCALIXARENE DERIVATIVES AND IMINECALIXARENE DERIVATIVES

(75) Inventors: Tae Sun Kim, Chuncheon-si (KR); Keum Soo Song, Chuncheon-si (KR); Hyung Sub Kim, Chuncheon-si (KR)

(73) Assignee: Biometrix Technology Inc., Chuncheon-si, Gangwon-do (KR)

( * ) Notice: Subject to any disclaimer, the term of this patent is extended or adjusted under 35 U.S.C. 154(b) by 838 days.

(21) Appl. No.: 12/266,480

(22) Filed: Nov. 6, 2008

(65) Prior Publication Data
US 2009/0191554 A1   Jul. 30, 2009

(30) Foreign Application Priority Data

Nov. 15, 2007  (KR) .................. 10-2007-0116371
Mar. 10, 2008  (KR) .................. 10-2008-0022048

(51) Int. Cl.
*A01N 33/02*  (2006.01)
*C12Q 1/70*   (2006.01)
*C12Q 1/68*   (2006.01)
*G01N 33/53*  (2006.01)

(52) U.S. Cl. .............. 514/646; 435/5; 435/6.1; 435/7.1; 435/7.2

(58) Field of Classification Search .................. 514/646; 435/5, 6, 7.1, 7.2, 6.1
See application file for complete search history.

(56) References Cited

U.S. PATENT DOCUMENTS

2001/0051714 A1   12/2001   Chen et al.
2003/0228974 A1   12/2003   Katz et al.

FOREIGN PATENT DOCUMENTS

| JP | 05-271175 A | 10/1993 |
| KR | 2002-0031734 A | 5/2002 |
| WO | WO 2007/043736 A1 | 4/2007 |
| WO | WO 2007/052879 A1 | 5/2007 |

OTHER PUBLICATIONS

Stratagene catalog, p. 39, 1988.*
PCT International Search Report for PCT/KR2008/001381, Mailing date of Aug. 14, 2008, 4 pages.
PCT Written Opinion of hte International Searching Authority for PCT/KR2008/001381, Mailing date of Aug. 14, 2008, 4 pages.

* cited by examiner

*Primary Examiner* — Jezia Riley
(74) *Attorney, Agent, or Firm* — Blakely, Sokoloff, Taylor & Zafman LLP

(57) ABSTRACT

Techniques for a surface-modified glass fiber with monolayer of aminocalixarene derivatives and iminecalixrene derivatives are provided.

17 Claims, 16 Drawing Sheets

X = the same as the functional groups representing the connecting parts having aldehyde terminal groups of formula 1

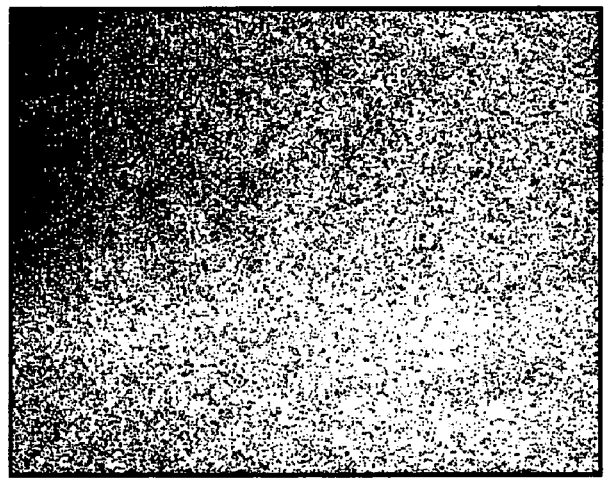
The glass fiber actually used in an illustrative embodiment
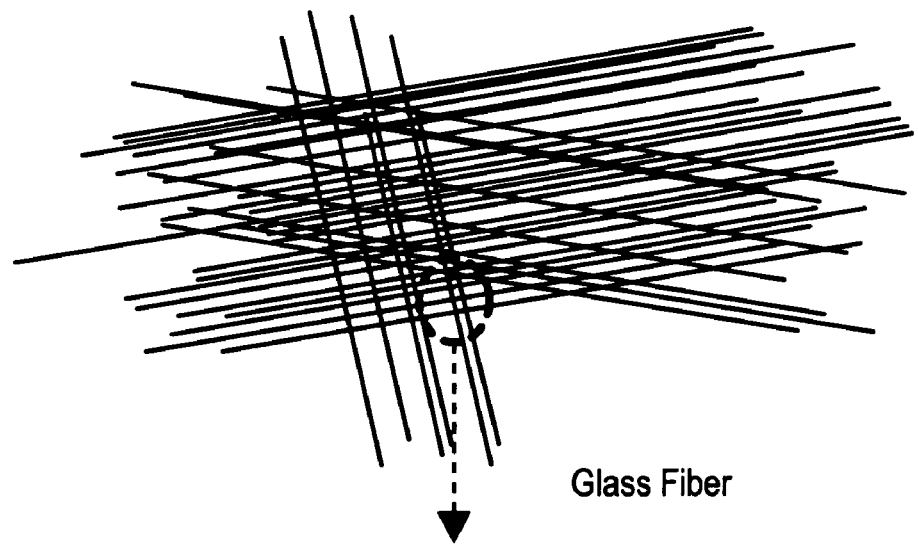
Glass Fiber
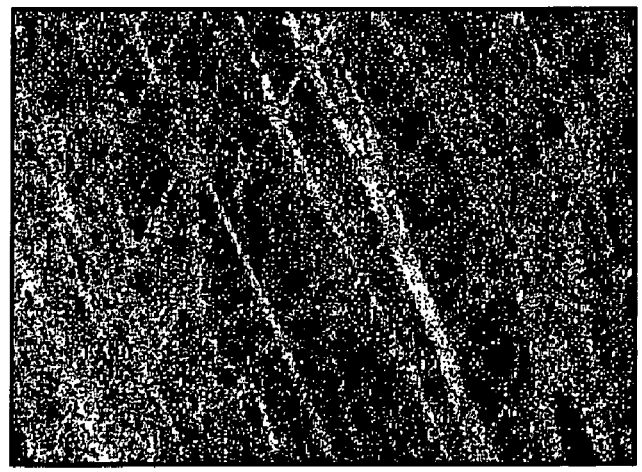
The enlargement of the surface of the glass fiber
FIG. 3

1. A line wherein a gene has a complementary base sequence
2. A line wherein a gene has a non-complementary base sequence
3. A line wherein a gene has a complementary base sequence

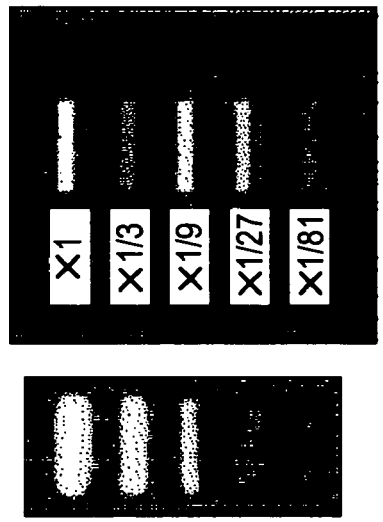
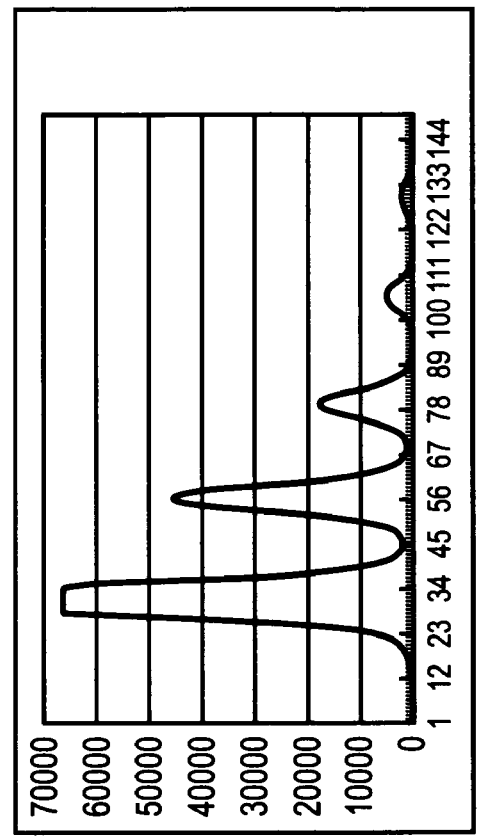
2. The theoretical immobilization amount of oligo-DNA wherein fluorescence-labeled target DNAs are coated on the surface and dried.
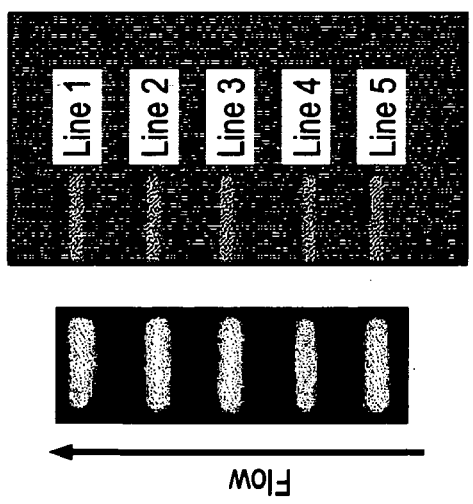
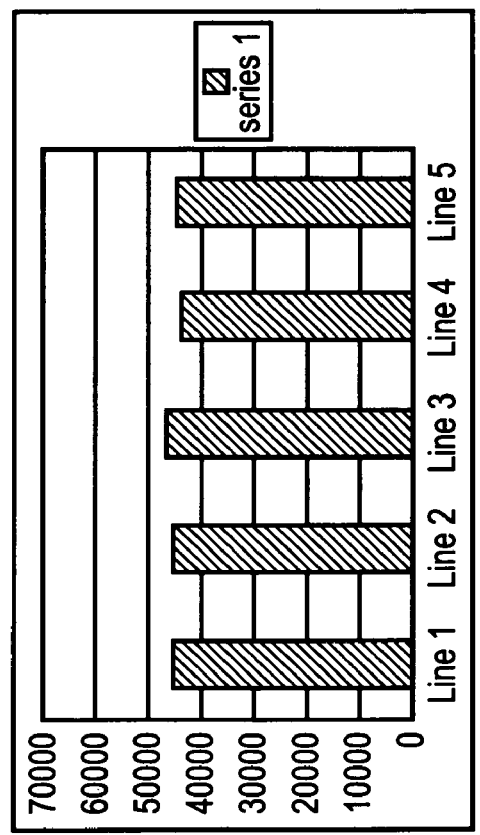
1. Actual experiment results wherein fluorescence-labeled target DNAs are hybridized.
FIG. 9

MODIFIED GLASS FIBER WITH MONOLAYER OF AMINOCALIXARENE DERIVATIVES AND IMINECALIXARENE DERIVATIVES

CROSS REFERENCE TO RELATED APPLICATIONS

The present application is based on, and claims priority from, Korean Patent Application No. 2007-116371, filed Nov. 15, 2007, and Korean Patent Application No. 2008-22048, filed Mar. 10, 2008, the disclosure of which is hereby incorporated by reference herein in its entirety.

BACKGROUND

Since a human genome map was completed in 2000 in a Human Genome Project conducted competitively by the Human Genome Research team and Celera Genomics, researches on the function of a gene and on the detection of a mutated gene have been done worldwide, and oligo DNA chips which is manufactured by using the results of the researches, where an oligomer DNA is bonded and immobilized and which is capable of genotyping various organisms, has been developed around the world.

Particularly, since a oligo DNA chip can genotype viruses, many researches have been done around the world on an oligo DNA chip prepared by immobilizing several oligo DNAs on a substrate of an oligo DNA chip, such as a DNA chip for accurately analyzing the route of a virus infection, confirming whether the virus is harmful or not, and predicting the possibility of cancer occurring by genotyping the virus group which causes cancer.

The DNA chip for genotyping HPV virus, which has been developed recently and spotlighted, is being developed as a DNA chip which can genotype dozens of types of human papiloma viruses (HPV). It is reported that in the case where a virus of a specific genotype is present, the chances of cervical cancer occurring in the future is higher than 90%. Accordingly, said chip has been recognized to be important as a bio chip for prevention of diseases which can predict the chances of a disease occurring, and as a result, has been granted an official permit by the Korea Food and Drug Administration for the first time in the world.

However, DNA chips prepared from modified glass slide where various DNAs are immobilized by using various physical and/or chemical methods go through user handling processes, such as loading, hybridization, washing, etc. In processing many samples by using human hands, there may be following problems, which need to be dealt with surely.

1) Human hands may not operate uniformly. In this regard, even a small difference in washing time or in the speed of dispensing an aqueous solution for washing, etc. may lead to a considerable error. Accordingly, the test results may change depending on the level of the person handling a DNA chip.

2) In a hybridization reaction conducted at a high temperature of about 50° C. for a long time of from about 30 minutes to about 2 hours, as a solvent evaporates, the number of bonding in the solution, e.g., the concentration of DNAs which could participate in the hybridization, increases sharply. In such case, the resulting signals may differ by several times, which makes difficult a positive/negative determination.

3) Particularly, there are cases where fluorescence is visible at a position where no fluorescence should be detected, thereby misleading to conclude that the corresponding DNA is present; that is, there are cases where nonspecific DNA expression occurs, which makes difficult precise genotyping.

4) In the case of a DNA chip, experiments on 4 to 8 samples are conducted in one DNA chip, and accordingly, there are often the cases where several coated solutions are mixed together, causing a serious problem that a sample which should be read negative reads positive. Accordingly, it is necessary to develop new genotyping technology where individual samples can be loaded and analyzed separately.

5) Particularly, a DNA chip based on a glass slide is difficult to manufacture in an easy to use form. Accordingly, it is necessary to develop technology which can produce an article maintaining a performance as a DNA chip and being manufactured in an easy to use form from a material having good processability.

6) In addition, one of the biggest factors preventing the wide use of a DNA chip is that, in order to confirm the final analysis result of the chip, an expensive scanner should be used. Most of the current scanners amount to tens of thousands of dollars, which has hindered the development and use of a DNA chip allowing genotyping of various viruses. In order to solve this problem, it is necessary to develop a genotyping strip which can carry out genotyping by using an analyzer of a low price between hundreds and thousands of dollars, and technology of modifying a glass fiber which is essential to manufacture such a strip, that is, a glass fiber which can immobilize DNAs and can be easily processed, and technology of immobilizing various DNAs on a modified glass fiber to allow analysis of various genes, that is, genotyping of various genes.

SUMMARY

In one embodiment, a method for preparing a surface-modified glass fiber includes bonding an aminocalixarene derivative or an iminecalixarene derivative on the surface of a glass fiber to form a monolayer.

In other embodiments, a method is provided for preparing a glass fiber, where oligo-DNAs are immobilized by immobilizing oligo-DNAs having consecutive guanine bases on the glass fiber prepared according to said method.

In another embodiments, a method is provided for preparing a rapid genotyping kit including using the glass fiber prepared according to said method, where various oligo-DNAs are immobilized to allow genotyping of various genes.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 3 is a picture of an illustrative embodiment of the glass fiber actually used for said preparation (Fusion 5 (Whatman Co., U.K.)), its enlargement, and its diagram, according to one embodiment. In some embodiments, a glass fiber may include a product by Whatman Co. of U.K., Water Co. of U.S.A. and Millipore Co. of U.S.A. etc. The glass fiber may be obtained by drawing a fine glass fiber with a diameter of 10 nm to several hundred μm from raw glass materials, and then weaving it into a membrane. Accordingly, said fiber may have a characteristic that a solvent applied on one side of the fiber develops by the force of gravity, the capillary action, microfluidics, or by a combination of at least two of thereof. The present embodiments use such characteristic of the glass fiber.

FIG. 8 shows the process of placing a glass fiber where multiple oligo-DNAs are immobilized in the form of lines into a strip and then injecting a solution including various genes through a sample inlet as in FIG. 7 and then, after a certain period, observing the amount of genes bonded to each of the lines with the naked eyes or by using an optical instrument, and then representing it as a magnitude of a signal. Genotypes of gene(s) present in the solution can be identified by observing the difference in the magnitude. In one embodiment, actual experiment results obtained by detecting fluorescence are presented in FIG. 6. From FIG. 6, it can be confirmed that considerable levels of fluorescence is detected only when the genotypes are identical.

FIG. 9 shows an illustrative embodiment of the results of actual experiments comparing the fluorescence intensity obtained when the theoretical maximum amounts of fluorescence-labeled genes that can be hybridized are coated and dried, with the fluorescence intensity obtained by hybridization with actually immobilized DNAs, according to one embodiment. Here, the theoretical maximum amount of fluorescence-labeled genes that can be hybridized may be obtained by calculating the maximum amount of oligo-DNAs having consecutive guanine bases which can be immobilized on the surface of a glass fiber when immobilizing the DNAs in the form of lines, and then calculating a maximum amount of fluorescence-labeled genes that can be hybridized with them. Here, this calculation may be made on the assumption that fluorescence-labeled genes are hybridized with the immobilized oligo-DNAs at 1:1 ratio (In order to confirm a decrease of fluorescence intensity from theoretical maximum amount i.e., ×1, fluorescence intensity may be measured using decreased concentrations of genes such as ×⅓, ×⅑, etc.). Meanwhile, the results of the experiment of hybridizing fluorescence-labeled genes with actually immobilized DNAs have been confirmed repeatedly by using 5 lines. The fluorescence intensity obtained from the experiment was about ⅓ times the theoretical maximum fluorescence intensity, which shows that the present embodiment achieves excellent gene immobilization and hybridization results.

FIG. 11 to FIG. 14 show the results obtained when applying amplified genes complementary to one probe genotype. FIG. 15 and FIG. 16 show the actual results obtained by applying amplified genes complementary to at least two probe genotypes and then carrying out the same method. All the results show that in genotyping using a modified glass fiber, genes are hybridized selectively, and nonspecific hybridization does not occur.

DETAILED DESCRIPTION

Figure 1:
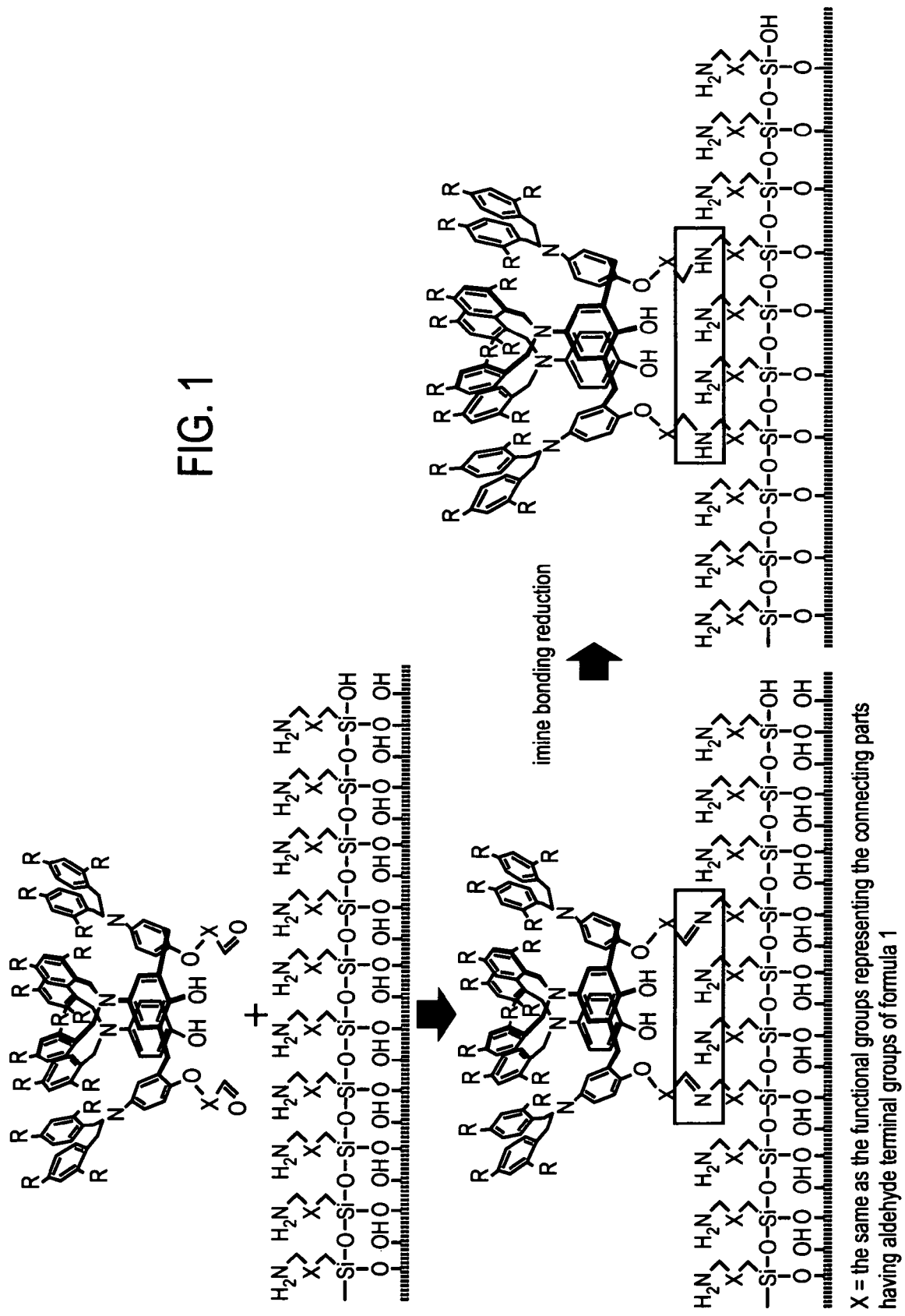
FIG. 1 and FIG. 2 are a diagram of an illustrative embodiment of the glass fiber whose surface is modified with amine according to the method of a paper published in Langmuir, 1996, Vol 12, pp 5338-5342, and a diagram showing the process of preparing a monolayer of macromolecules by bonding the derivative of formula 1 or formula 2 with the amine-modified glass fiber, according to one embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the components of the present disclosure, as generally described herein, and illustrated in the Figures, may be arranged, substituted, combined, and designed in a wide variety of different configurations, all of which are explicitly contemplated and make part of this disclosure.

In order to solve the problem of the conventional DNA chips prepared by immobilizing oligo-DNAs on a glass slide, some embodiments adopt the following methods.

In one embodiment, the research team of the present disclosure has developed technology of preparing a glass slide where oligo-DNAs having 7~15 consecutive guanine bases are spontaneously immobilized. Such a glass slide is prepared by applying an aminocalixarene derivative of formula 1 and an iminecalixarene derivative of formula 2 to an amine-modified glass slide to form an aminocalixarene monolayer and an iminecalixarene monolayer, respectively. In case of coating oligo-DNAs in the form of a solution on this glass slide, various kinds of oligo-DNAs are spontaneously immobilized. Accordingly, this glass slide is used to prepare a DNA chip easily and with high reproducibility.

In one embodiment, in order to immobilize various DNAs on a glass fiber, the present embodiment uses a fact that properties of a surface of a glass fiber is the same as that of a glass slide. The present embodiment modifies a surface of a glass fiber with amine according to the known method disclosed in *Langmuir*, 1996, Vol 12, pp 5338-5342. Then, the present embodiment applies an aminocalixarene derivative of formula 1 and/or an iminecalixarene derivative of formula 2 to an amine-modified glass fiber to form an aminocalixarene monolayer and/or an iminecalixarene monolayer, respectively. Then, a surface of a glass fiber is coated with a solution including DNAs in the same way as for a glass slide to prepare a glass fiber where DNA is immobilized. The present embodiment is aimed at establishing technology of preparing a glass fiber where several DNAs are immobilized, and a method of preparing a genotyping strip using the glass fiber. In other embodiment, a technology is provided for preparing a genotyping strip, which identifies a genotype by bonding one or more of genes or a product obtained by subjecting the solution to a polymerase chain reaction (PCR) in a solution with a probe DNA bonded onto a glass fiber by hybridization.

Figure 2:
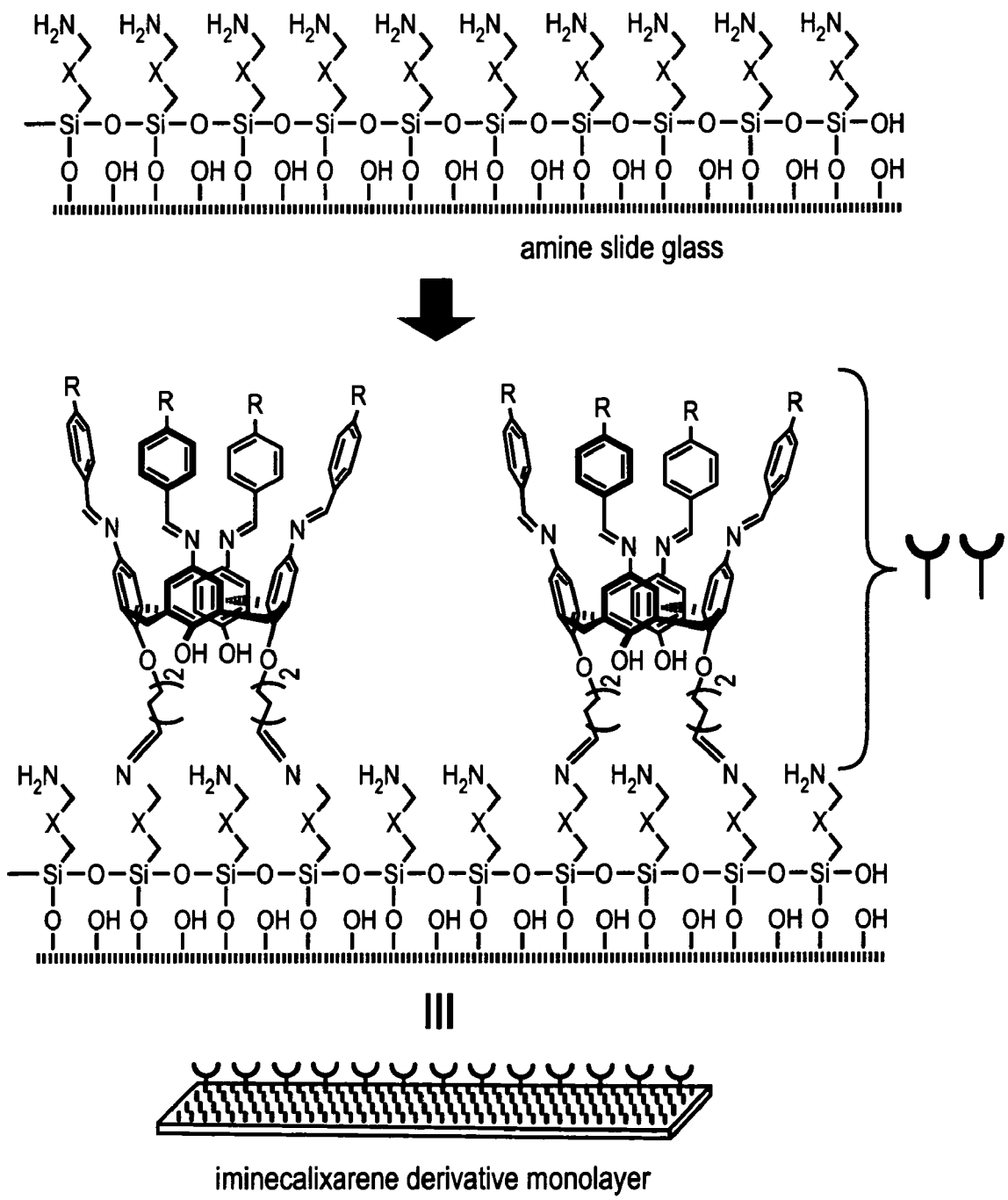

In one embodiment, a method is provided for the preparation of a surface-modified glass fiber, where said glass fiber is prepared by bonding an aminocalixarene derivative of formula 1 and an iminecalixarene derivative of formula 2 onto the surface of an amine-modified glass fiber according to the method of FIGS. 1 and 2, to form a monolayer.

$Y_1, Y_2, Y_3$ and $Y_4$ are independently selected from the group consisting of —H, —$(CH_2)_n$—CH=O, —$(CH_2)_n$—SH, —$(CH_2CH_2O)_m$—$CH_2CH_2$—CH=O, —$(CH_2CH_2O)_m$—$CH_2CH_2$—SH, —$(CH_2)_m$—$C_6H_4$—$(CH_2)_c$-Z and —CO—$(CH_2)_{m-1}$—$C_6H_4$—$(CH_2)_c$-Z, where, n=2~15, m=1~10, c=0~10, Z is a group selected from the group consisting of —SH, —CHO, —COOH and —$NH_2$, and —$C_6H_4$— and —$C_6H_5$ are defined as phenyl group.

[formula 2]

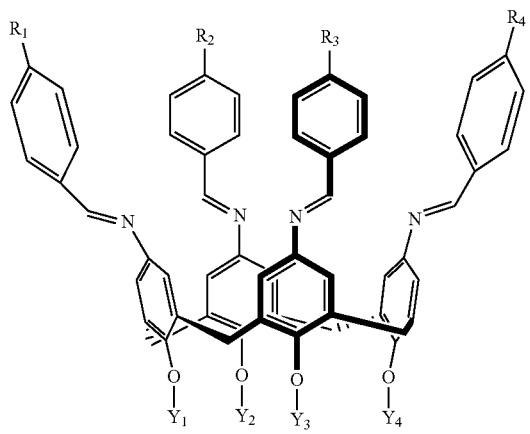

where, $R_1, R_2, R_3$ and $R_4$ are independently selected from the group consisting of —H, —$CH_3$, —$C_2H_5$, —$C_3H_7$, —$OCH_3$, —Cl, —$C_6H_5$, —OH, —$OCH_2CH_3$, —Br, —$CF_3$, —$OCH_2C_6H_5$, —$OC_6H_5$, —$OC_6H_4CH_3$, —$OC_6H_4C$

[formula 1]

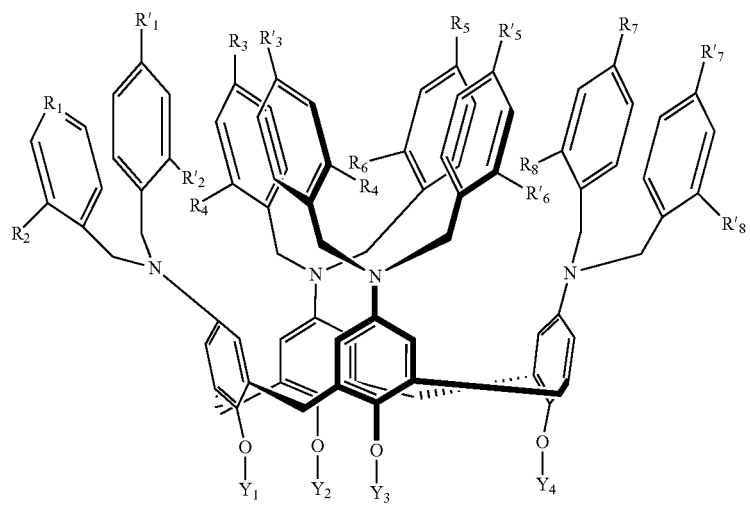

where, $R_1, R_2, R_3, R_4, R_5, R_6, R_7, R_8, R'_1, R'_2, R'_3, R'_4, R'_5, R'_6, R'_7$ and $R'_8$ are independently selected from the group consisting of —H, —$CH_3$, —$C_2H_5$, —$C_3H_7$, —$OCH_3$, —Cl, —$C_6H_5$, —OH, —$OCH_2CH_3$, —Br, —$CF_3$, —$OCH_2C_6H_5$, —$OC_6H_5$, —$OC_6H_4CH_3$, —$OC_6H_4C$ $(CH_3)_3$, —$OC_6H_4CF_3$, —$OC_6H_4Cl$, —$OCOCH_3$, —NHCOCH_3, —CONHCH_3, —CN, COOH, and —COOR where R represents —$CH_3$ or —$C_2H_5$;

$(CH_3)_3$, —$OC_6H_4CF_3$, —$OC_6H_4Cl$, —$OCOCH_3$, —NHCOCH_3, —CONHCH_3, —CN, COOH, and —COOR where R represents —$CH_3$ or —$C_2H_5$;

$Y_1, Y_2, Y_3$ and $Y_4$ are independently selected from the group consisting of —H, —$(CH_2)_n$—CH=O, —$(CH_2)_n$—SH, —$(CH_2CH_2O)_m$—$CH_2CH_2$—CH=O, —$(CH_2CH_2O)_m$—$CH_2CH_2$—SH, —$(CH_2)_m$—$C_6H_4$—$(CH_2)_c$-Z and —CO—$(CH_2)_{m-1}$—$C_6H_4$—$(CH_2)_c$-Z, where, n=2~15, m=1~10, c=0~10, Z is a group selected from the group consisting of —SH, —CHO, —COOH and —NH$_2$, and —C$_6$H$_4$— and —C$_6$H$_5$ are defined as phenyl group.

In some embodiments, the aminocalixarene derivative of formula 1 and the iminecalixarene derivative of formula 2 may be prepared according to the method disclosed in Korean Patent Application Nos. 10-2005-0096322, 10-2005-0103857, 10-2005-0105340 and 10-2005-0110824, which are incorporated herein by reference.

In one embodiment, with regard to the method for forming a monolayer on a glass fiber, as described in the explanation of FIG. 3, a glass fiber has a thickness from about 10 nm to several hundred μm, and a glass fiber whose surface is abundant with a silanol (—SiOH) function group is modified to be a glass fiber having an amine terminal by a chemical reaction (Refer to Langmuir, 1997, Vol 13, pp 4305-4308; Langmuir, 1996, Vol 12, pp 5338-5342). Then, the glass fiber having an amine terminal may be immersed in a solution where the compound of formula 1 or 2 is dissolved in a concentration of 0.1~5.0 mM in an organic solvent such as CHCl$_3$, etc, for about 1 to about 24 hours. Then, the glass fiber may be washed with the same solvent and dried to obtain a surface-modified glass fiber where a monolayer of aminocalixarene or iminecalixarene is formed.

By using said method, one illustrative embodiment provides a glass fiber having a self-assembled monolayer, where an aminocalixarene derivative of formula 1 or an iminecalixarene derivative of formula 2 is attached to a surface of a glass fiber by a chemical bonding such as an imine bonding, an amine bonding obtained by reducing imine bonding, a thiol bonding, an ester bonding, an ether bonding, an amide bonding, etc.

Figure 4:
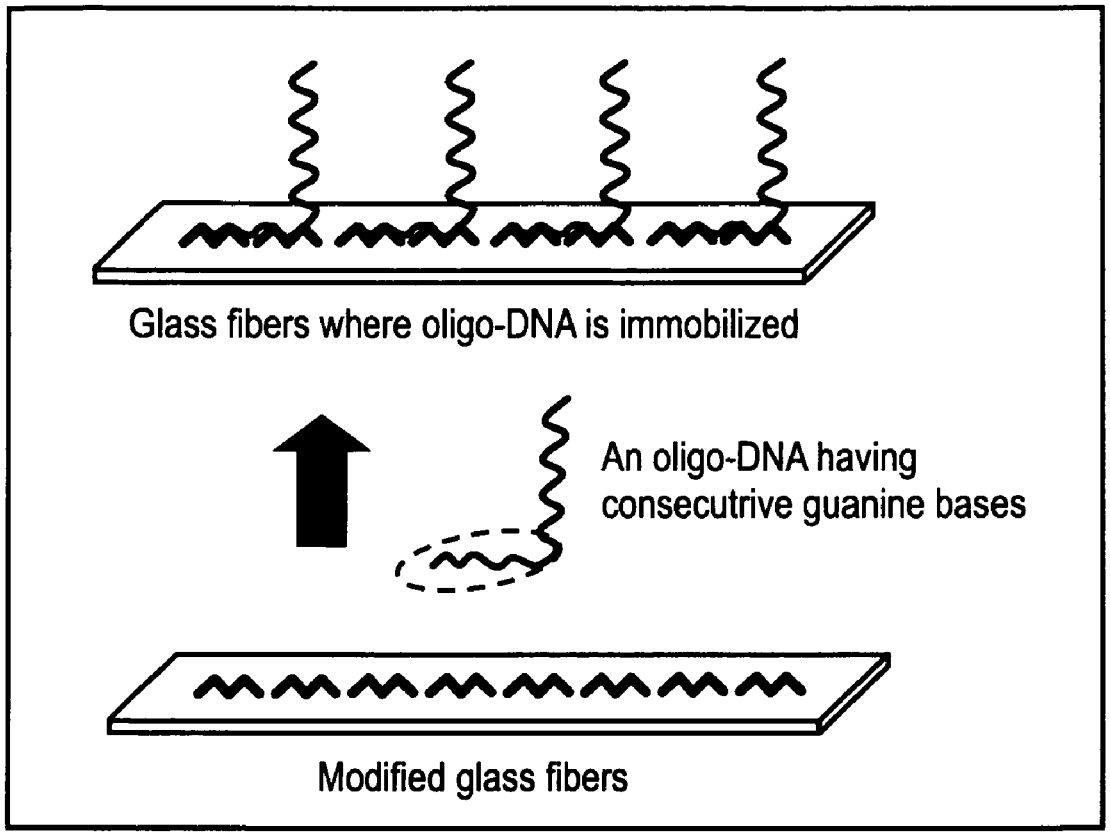
FIG. 4 is a diagram showing an illustrative embodiment of the process of preparing glass fibers where oligo-DNA is immobilized by dispensing a solution where oligo-DNA having consecutive guanine bases is dissolved in the form of a line with a specific width on a glass fiber modified with a monolayer of macromolecules, by using a dispenser, etc, according to one embodiment.
Figure 5:
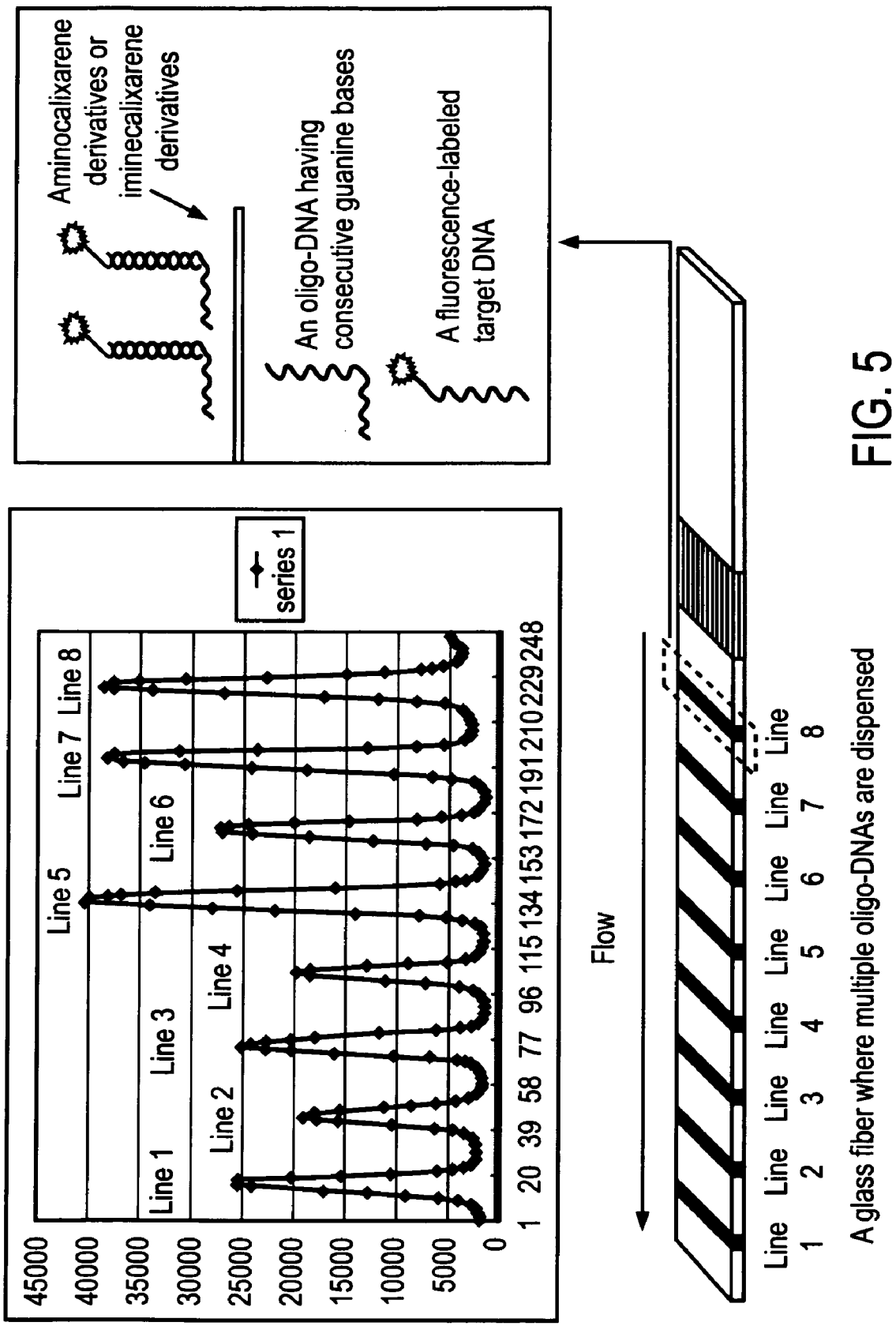
FIG. 5 shows an illustrative embodiment of the result of an actual experiment, according to one embodiment. In this experiment, when a solution including a fluorescence-labeled amplified gene obtained by a polymerase chain reaction (PCR) is applied on a glass fiber where oligo-DNAs having consecutive guanine bases are coated in the form of lines, and as a result, where multiple oligo-DNAs are immobilized in the form of multiple lines, the solution develops by itself, and then genes of which genotypes are complementary to the immobilized probe oligo-DNAs are bonded by hybridization. This experiment used fluorescence-labeled genes in order to identify the bonded genes by measuring fluorescence intensity.

In some embodiments, in a method of immobilizing DNA onto a modified glass fiber illustrated in FIGS. 4 and 5, oligo-DNAs having consecutive guanine bases may be spontaneously immobilized in an immobilization solution where 60-600 mM of ions are present to prepare a glass fiber where DNA is immobilized. In one embodiment, a method of immobilizing DNA includes: preparing an immobilization solution by dissolving an oligo-DNA having consecutive guanine bases (e.g. 9 consecutive guanine bases) in a BMT dispensing solution (solution of 600 mM of ammonium ions); dispensing said immobilization solution to said glass fiber modified with a monolayer of aminocalixarene or iminecalixarene; and immobilizing the oligo-DNA. Said method may optionally include washing said glass fiber, and blocking the locations except those where oligo-DNA is immobilized. In other embodiments, the immobilization step may be conducted at the room temperature for about 1 to about 4 hours. In another embodiment, the blocking step may include putting the washed glass fiber into a blocking solution (1×~4×SSC, 0.1-5.0% caseine) and treating it for 10~30 minutes.

Figure 6:
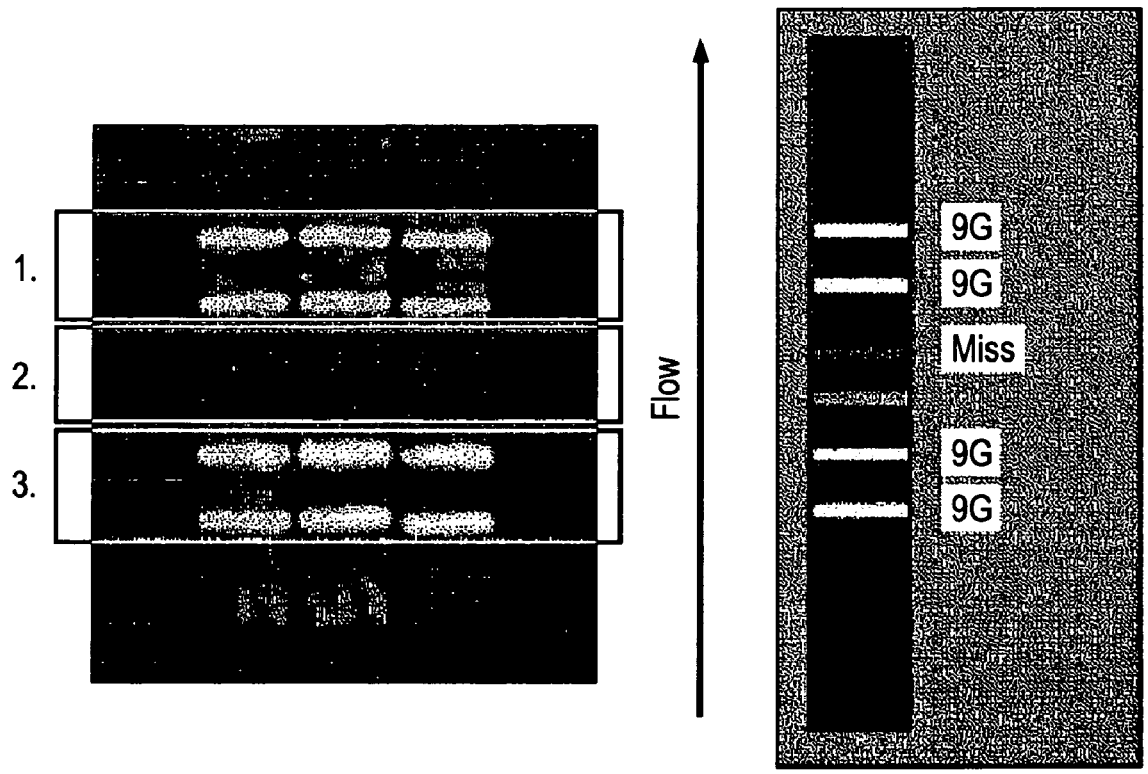
FIG. 6 shows an illustrative embodiment of actual experiment results obtained by letting a solution including fluorescence-labeled genes flow on a glass fiber where multiple oligo-DNAs are coated in the form of lines to be immobilized, and conducting an analysis by using a fluorescence scanner, according to one embodiment. Strong fluorescence is detected at locations where the base sequences of the genes are identical with base sequences desired to be detected, and no fluorescence is detected at locations where the base sequences are not identical with base sequences desired to be detected. Thus, in this experiment, fluorescence-labeled genes are detected only at locations where the base sequences are identical.

When compared according to the method of FIG. 9, it was observed that the concentration of the DNAs immobilized onto the thus-prepared glass fiber is about ½ to ⅓ times of the theoretical maximum immobilization amount, which shows that the present embodiment achieved technology of preparing a glass fiber capable of immobilizing DNA in an amount near the theoretical maximum. FIG. 5 and FIG. 6 show an illustrative embodiment of the hybridization results of various genes according to the degree of consistency of the bases. In one embodiment, DNAs were immobilized into 8 straight lines in a narrow space of about 1.4 cm, and then each line was coated with a fluorescence-labeled gene to conduct hybridization. In one embodiment, a glass fiber may firmly immobilize DNAs in an amount such that the fluorescence is individually identified at the immobilized location by hybridization, to maintain a spaced state and its immobilized location while a solution develops, which is shown in the experiment result in FIG. 5. Example 3 shows an illustrative embodiment of a method of immobilizing DNAs, and Example 4 shows an illustrative embodiment of a process of coating fluorescence-labeled genes.

In other embodiment, a method is provided for genotyping capable of identifying a gene having a specific base sequence, including:
developing a solution including fluorescence-labeled genes having an amplified nucleic acid, over the glass fiber; and
bonding genes having a specific base sequence, e.g., a specific genotype of virus, with a complementary probe oligo-DNAs immobilized on the surface of the glass fiber by hybridization.

FIG. 6 shows an illustrative embodiment of a result in genotyping, i.e., the hybridization result according to the consistency of genes. In one embodiment, several genes of different genotypes are immobilized and a fluorescence-labeled gene of one genotype is coated according to Example 5, in order to obtain the hybridization results. FIG. 6 presents an illustrative embodiment of actual experimental results and analysis of the results. According to the results, the location where the genotypes do not match shows little fluorescene intensity, but the location where the genotypes match shows 10 to 40 times higher fluorescence intensity.

In one embodiment, a method for genotyping may be carried out at a low temperature from about 4° C. to about 20° C., at a room temperature from about 20° C. to about 30° C. according to other embodiment, and at a high temperature from about 30° C. to about 60° C. according to another embodiment. Meanwhile, since the polymerase chain reaction was disclosed in 1971 by K. Kleppe and G, Khorana in *the Journal of Molecular Biology*, vol. 56, pp 341~361, the hybridization of amplified gene has been conventionally conducted at a high temperature from about 40° C. to about 60° C. to increase selectivity. However, a result of the reaction carried out at a normal temperature as in the present application has not been published. Generally, the temperature of a lab is maintained at about 22° C. to 25° C., and hybridization may be carried out at a room temperature including said temperature, according to some embodiments. In the case of a hybridization reaction that can be carried out only at a high temperature (from about 30° C. to about 60° C.), hybridization can be carried out only when the temperature is raised by using an oven, etc. In the case of a hybridization reaction carried out at a low temperature (from about 4° C. to about 20° C.), hybridization is carried out while using a device for lowering the temperature, such as a chiller. Hybridization may be categorized according to the reaction temperature and a device for maintaining the temperature.

In the present disclosure, a glass fiber is modified with macromolecules such that probe DNAs having consecutive guanine bases can be immobilized on the glass fiber. In addition, in the present disclosure, the probe oligo-DNAs are appropriately spaced from each other by the consecutive guanine bases, thereby making it possible to carry out hybridization even at a room temperature or a low temperature. Different from general expectation, the probe DNA immobilized on the modified glass fiber is hybridized at a room temperature or a low temperature, and obtains fluorescence intensity showing that the same or higher hybridization rate than in the hybridization at a high temperature has been illustrate. In some embodiments, FIG. 6 and FIG. 9 illustrate, a fluorescence data obtained from hybridization at a room temperature, which can be easily used, among various fluorescence data.

In addition, compared with the data obtained from a DNA chip based on conventional glass slide, the present embodiment provides a modified glass fiber having remarkably excellent selectivity and reduced nonspecificity, and technology of preparing and using a strip for rapid genotyping (e.g., virus genotyping strip) by using said glass fiber. In one embodiment, a genotyping strip may include a glass fiber including at least one type of oligo-DNA having consecutive guanine bases, and may have a sample inlet on a part of the glass fiber on which oligo-DNA is not immobilized. The genotyping strip may be prepared in the form of a rapid strip or a genotyping kit including the strip.

In some embodiments, a method is provided for genotyping capable of identifying a gene having a specific base sequence, including:

injecting a solution including fluorescence-labeled genes having an amplified nucleic acid, through the sample inlet of the strip for genotyping according to the present embodiment;

developing the solution over the glass fiber; and bonding genes having a specific base sequence with a complementary probe oligo-DNAs immobilized on the surface of the glass fiber by hybridization.

In another embodiment, a method is provided for genotyping, including: coating a glass fiber with a solution including genes (RNA, DNA, etc.) having specific sequences; bonding the genes having a specific base sequence with a complementary oligo-DNAs having consecutive guanine bases immobilized on a surface of a glass fiber by hybridization; and measuring the total amount of the bonded genes by spectroscopic methods using fluorescence, or visible rays, etc.

To sum up, the present disclosure provides a glass fiber modified with macromolecules, where oligo-DNAs are immobilized, the preparation method thereof, and the method of preparing a genotyping strip using said glass fiber where oligo-DNAs are immobilized. In addition, the present disclosure achieved technology of preparing and using a surface-modified glass fiber where oligo-DNAs are immobilized. The present disclosure can solve the problems that a conventional DNA chip cannot be widely used due to the use of an expensive scanner, and the test results change depending on the person who uses the chip, and the chip is not easy to handle. In addition, the present disclosure achieved technology of preparing a genotyping strip which is easy to use and requires little processing, etc, thereby can remarkably improve problems occurring with a DNA chip based on a conventional glass slide and suffered by many users. In addition, a glass fiber has a characteristic that a solution develops thereon at a specific speed, as in NC(nitrocellulose) membrane used for a rapid kit. Accordingly, when oligo-DNA is immobilized on a surface of a glass fiber, gene included in a solution developing at a specific speed is hybridized while developing through the uniformly immobilized DNAs at a constant speed. Accordingly, the present embodiment can prepare an article in the form of a strip, which does not need to be handled by a user except when injecting a sample in the form of a solution. As such, the present embodiment provides a chip that can be used without a user handling, thereby can remarkably increase the reproductibility of test results and increase convenience. In order to achieve the above effects, the present inventors have developed technology of modifying the surface of a glass fiber by immobilizing the oligo-DNA.

Thus, the present embodiment provides world's first technology of preparing glass fiber by improving conventional technology of modifying a glass slide, thereby making it possible to prepare a genotyping strip where oligo-DNA is immobilized with a high density such that it can be used without user handling. In addition, the present embodiment achieved technology of preparing a genotyping strip using a glass fiber where oligo-DNA is immobilized. Not only the strip prepared according to this technology can solve the problem occurring when preparing and using conventional oligo-DNA chips, such as that the test results are not reproducible and that the test results change depending on the user, but also can provide technology of preparing a DNA chip in the form of a glass fiber-based strip, thereby allowing genotyping using an inexpensive analyzer (i.e., without using an expensive analyzer costing tens of thousands of dollars). The present embodiment can solve most of the problems occurring when preparing and using a DNA chip based on a conventional glass slide. Test results of the thus-prepared strip can be obtained by using a scanner of a low price of about hundreds of dollars to thousands of dollars equipped with a linear motor. FIG. 5 shows an illustrative embodiment of a graph of actual experimental results obtained by a low-price scanner. The present embodiment is important in that it can solve the problem occurring when using conventional DNA chips to allow various diagnosis using genotyping.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed invention. Additionally the phrase "consisting essentially of" will be understood to include those elements specifically recited and those additional elements that do not materially affect the basic and novel characteristics of the claimed invention. The phrase "consisting of" excludes any element not specifically specified.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present embodiments, thus generally described, will be understood more readily by reference to the following examples, which are provided by way of illustration and are not intended to be limiting of the present technology in any way.

EXAMPLES

The present technology is further illustrated by the following examples, which should not be construed as limiting in any way.

Example 1

Method for Forming a Monolayer on an Amine-Modified Glass Fiber by Applying a Solution where 5,11,17,23-tetradibenzylaminocalix[4]arene-1,3-hexanealdehyde (TDBACAHA) is Dissolved

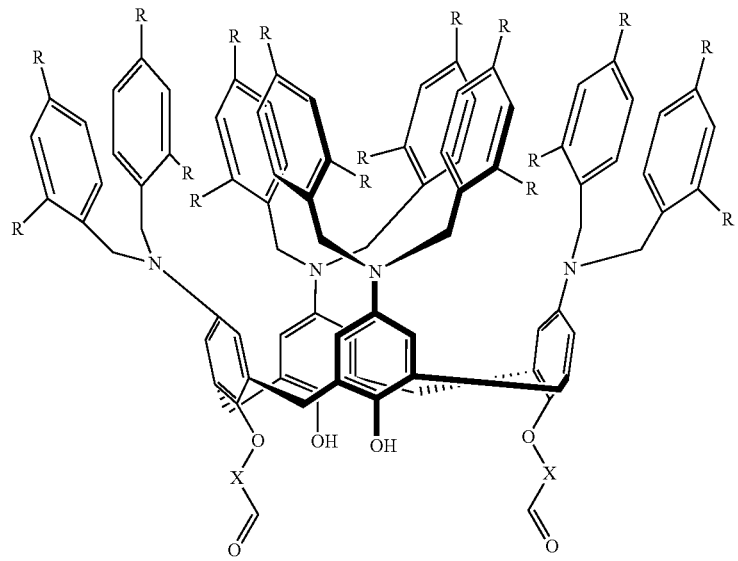

where X is the same as the functional group representing the connecting parts having aldehyde terminal groups of formula 1

TDBACAHA

In an illustrative embodiment, 0.1~5.0 mM of 5,11,17,23-tetradibenzylaminocalix[4]arene-1,3-hexanealdehyde (TDBACAHA) among the derivatives of formula 1 was dissolved in an organic solvent such as $CHCl_3$ etc. to prepare a solution. As shown in FIG. 1, a glass fiber where amine functional groups are attached (e.g., amine glass fiber substrate) was immersed in the thus-prepared solution for 1-24 hours, and then the glass fiber was sequentially washed with chloroform, acetone, and then finally with water, and then dried to form the aminocalixarene monolayer. Another aminocalixarene derivative monolayer was prepared according to the same method.

Example 2

Method of Modifying an Amine-Modified Glass Fiber by Applying a Solution where 5,11,17,23-tetrabenzyliminealkoxycalix[4]arene (TBICOCA) is Dissolved

TBICOCA

In an illustrative embodiment, 0.1~5.0 mM of 5,11,17,23-tetrabenzyliminealkoxycalix[4]arene (TBICOCA) among the derivatives of formula 2 was dissolved in an organic solvent such as $CHCl_3$ etc. to prepare a solution. As shown in FIG. 2, a glass fiber where amine functional groups are attached (e.g., amineglass fiber substrate) was immersed in the thus-prepared solution for 1-24 hours, and then the glass fiber was sequentially washed with chloroform, acetone, and then finally with water, and then dried to form the iminecalixarene monolayer. Another iminecalixarene derivative monolayer was prepared according to the same method.

Example 3

Method of Immobilizing Oligo-DNAs by Using a Modified Glass Fiber to Genotype Various Types of Genes In an illustrative embodiment, a Biodot dispenser (Model No. XYZ 3050, U.S.A) was used for the oligo-DNA immobilization shown in FIG. 5. In order to genotype various types of genes, probe DNAs having completely complementary base sequence as listed in Table 1 was immobilized as in FIG. 5. That is, 3-30 pmol/μℓ of oligo-DNAs having consecutive 9 guanine bases were dissolved in a BMT dispensing solution (600 mM ammonium ion solution) to prepare 8 sets of an immobilization solution (600 mM ammonium ion solution; product name: BMT spotting solution-9G, manufactured by Biomatrix Technology Co. of Republic of South Korea). Said immobilization solution was dispensed at the rate of 5-50 mm/sec by using a dispensing nozzle. On a modified glass substrate (glass fiber), an aminocalixarene derivative monolayer or an iminecalixarene derivative monolayer as shown in FIG. 4 was formed according to the methods of Examples 1 and 2. Then, oligo-DNAs were immobilized in the form of lines of 0.5-5 mm in width on the thus-prepared glass substrate. After carrying out immobilization for 1~4 hours at the room temperature, the glass fiber was washed, and then immersed into 250 μℓ of BMT blocking solution (1x~4xSSC, 0.1-5.0% caseine; product name: BMT Blocking solution-9G, Biomatrix Technology Co., Republic of South Korea) for 10~30 minutes in order to block the locations where oligo-DNAs are not immobilized.

TABLE 1

| Probe name | Base sequence (5'-3') | Description |
|---|---|---|
| 9G | GGGGGGGGGAAATCAACCCACAGCTG CA | Probe DNA having the complementary base sequence |
| Cy5 DNA | Cy5-GTG CAG CTG TGG GTT GAT T-3 | Fluorescence-labeled target DNA |

Example 4

Method of Detecting Gene by Using Hybridization with a Fluorescence-Labeled Target DNA In an illustrative embodiment, in order to carry out hybridization with a fluorescence-labeled target DNA, 5 μℓ of fluorescence-labeled target DNA listed in Table 1 and 75 μℓ of BMT hyb-mixA (6xSSC, 20% formamide, 0.05% triton X-100; product name: BMT Hyb-solution-9G, Biomatrix Technology Co., Republic of South Korea) were put into a 1.5 μℓ tube to prepare 80 μℓ of a mixed solution. Then, the thus-prepared solution was injected through the sample inlet of an assembled strip. Then, hybridization was carried out at a room temperature (20±5° C.) for 5~50 minutes. After hybridization has been completed, 100~300 μℓ of 0.1x~4xSSC solution was injected and then the strip was separated. Then, the glass fiber was attached to a slide and then the fluorescence intensity was analyzed quantitatively by using a microarray scanner (GSI Lumonics, U.S.A.) or a linear scanner. FIG. 5 illustrates an illustrative embodiment of actual experiment results obtained by using a linear scanner. These results show that a glass fiber where oligo-DNAs are immobilized has been prepared, and that when applying various types of genes on a surface-modified glass fiber and then letting a solution including a fluorescence-labeled target DNA flow over the glass fiber, genes in the solution are hybridized with various immobilized oligo-DNAs, and thereby the glass fiber can identify whether a specific type of gene is included in the solution.

Example 5

Experiment of Detecting a Specific Type of Gene by Using a Surface-Modified Glass Fiber In an illustrative embodiment, in the oligo-DNA immobilization shown in FIG. 6, a Biodot dispenser (Model No. XYZ 3050, U.S.A.) was used. In order to determine nonspecific fluorescence, the probe oligo-DNAs having a completely complementary base sequence and the probe oligo-DNAs having a non-complementary base sequence as listed in Table 2 were immobilized as shown in FIG. 6 according to the method of FIG. 4. The same composition of an immobilization solution and the same dispensing method as those of Example 3 were used to prepare a glass fiber where DNAs are immobilized.

TABLE 2

| Probe name | Base sequence (5'-3') | Description |
|---|---|---|
| 9G | GGGGGGGGGAAATCAACCCACA GCTGCA | Probe oligo-DNA having a complementary base sequence |
| M | GGGGGGGGGAGTTCAAATTATT TTCCTA | Probe oligo-DNA having a non-complementary base sequence |
| Cy5-DNA | Cy5-GTG CAG CTG TGG GTT GAT T-3 | Fluorescence-labeled target DNA |

Figure 10:
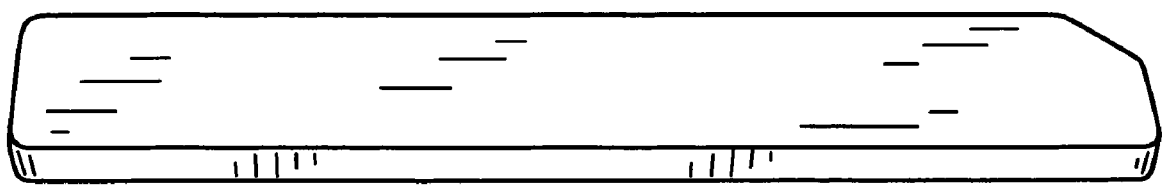
FIG. 10 is a picture showing an illustrative embodiment of the type of an assembled strip having a sample inlet, as used in FIG. 7 and FIG. 8, according to one embodiment.
Figure 11:
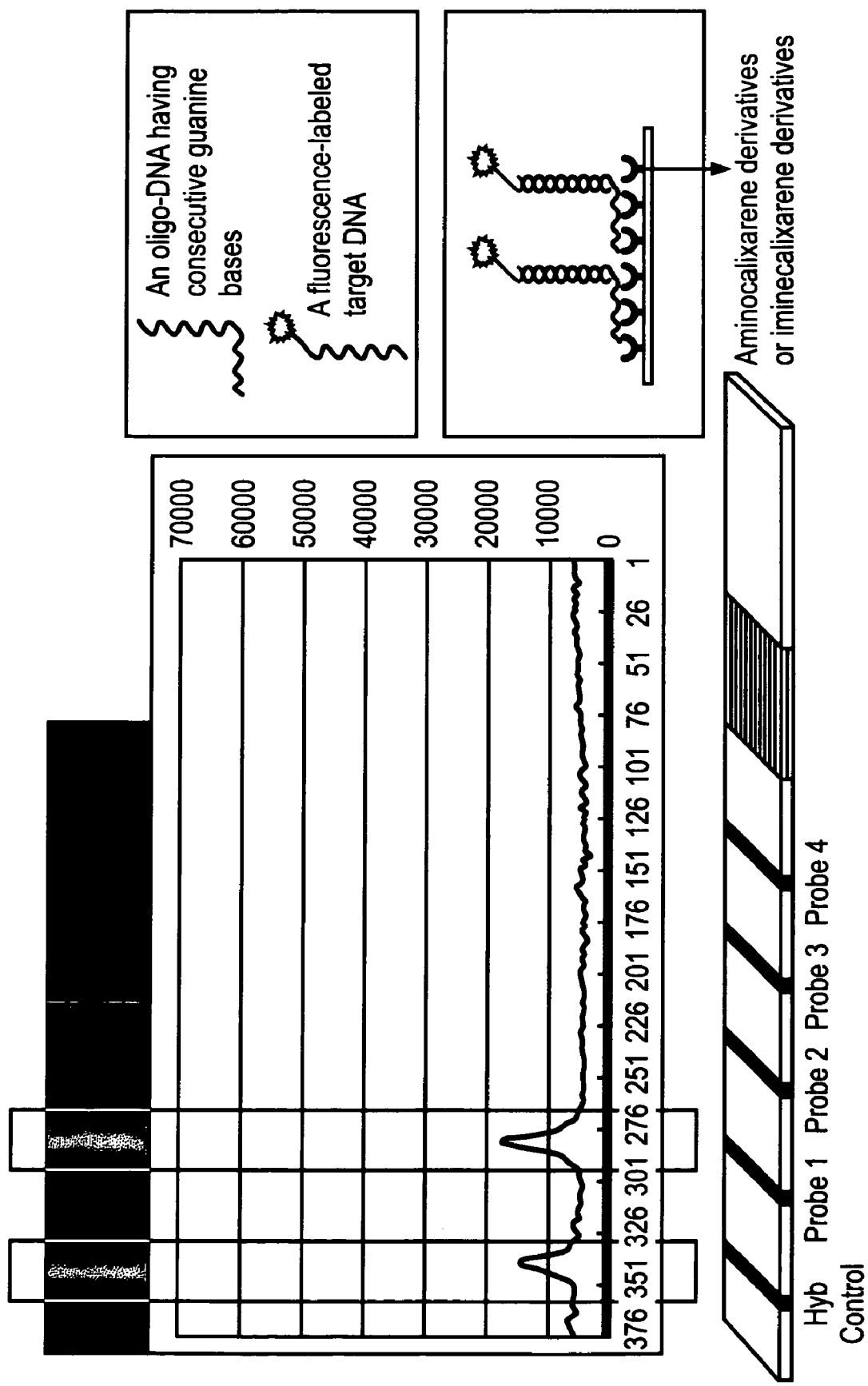
FIG. 11 to FIG. 16 show illustrative embodiments of the experiment result obtained by assembling a modified glass fiber where probe oligo-DNAs of different genotypes are immobilized into a strip as shown in FIG. 10, and then letting fluorescence-labeled amplified genes develop on the strip, and then reading the result by using a fluorescence scanner as described in Example 7, according to some embodiments.
Figure 12:
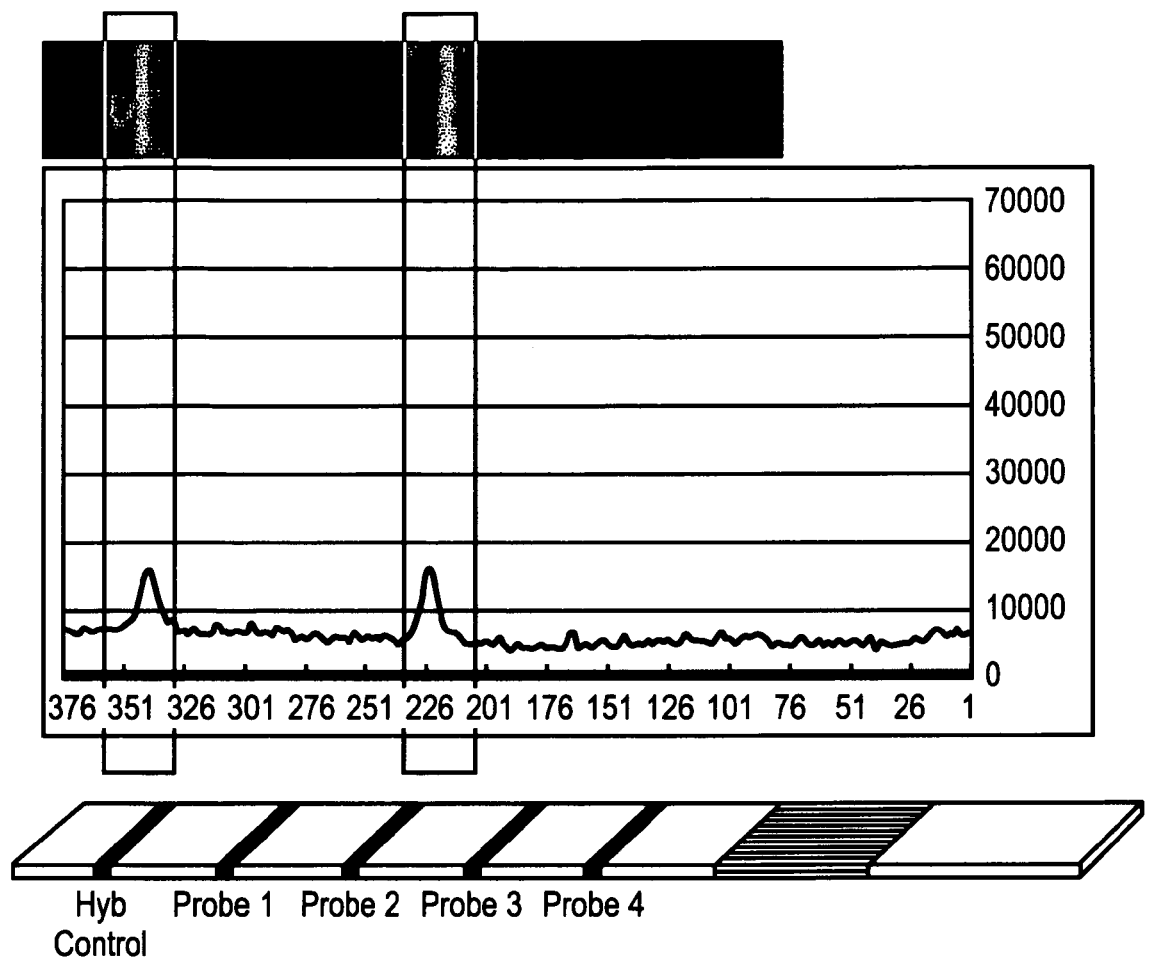
Figure 13:
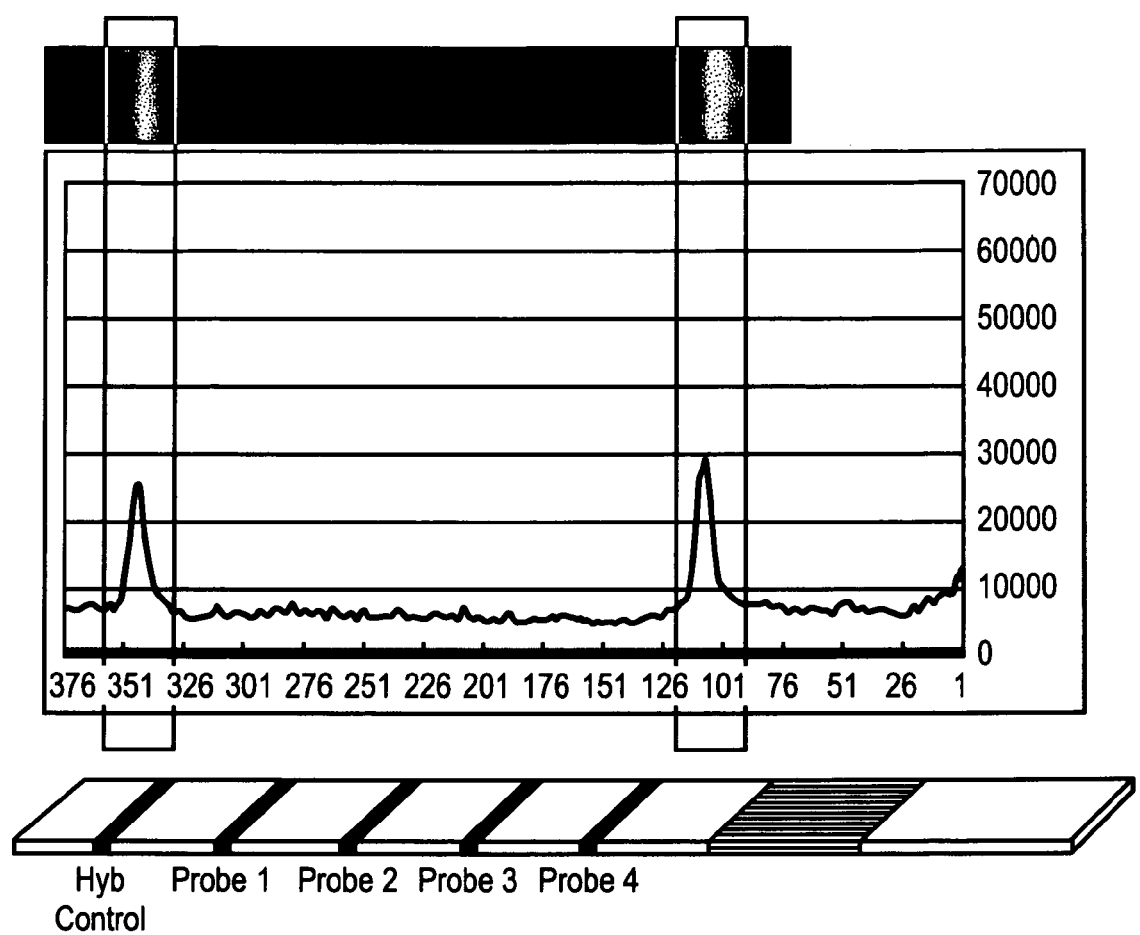
Figure 14:
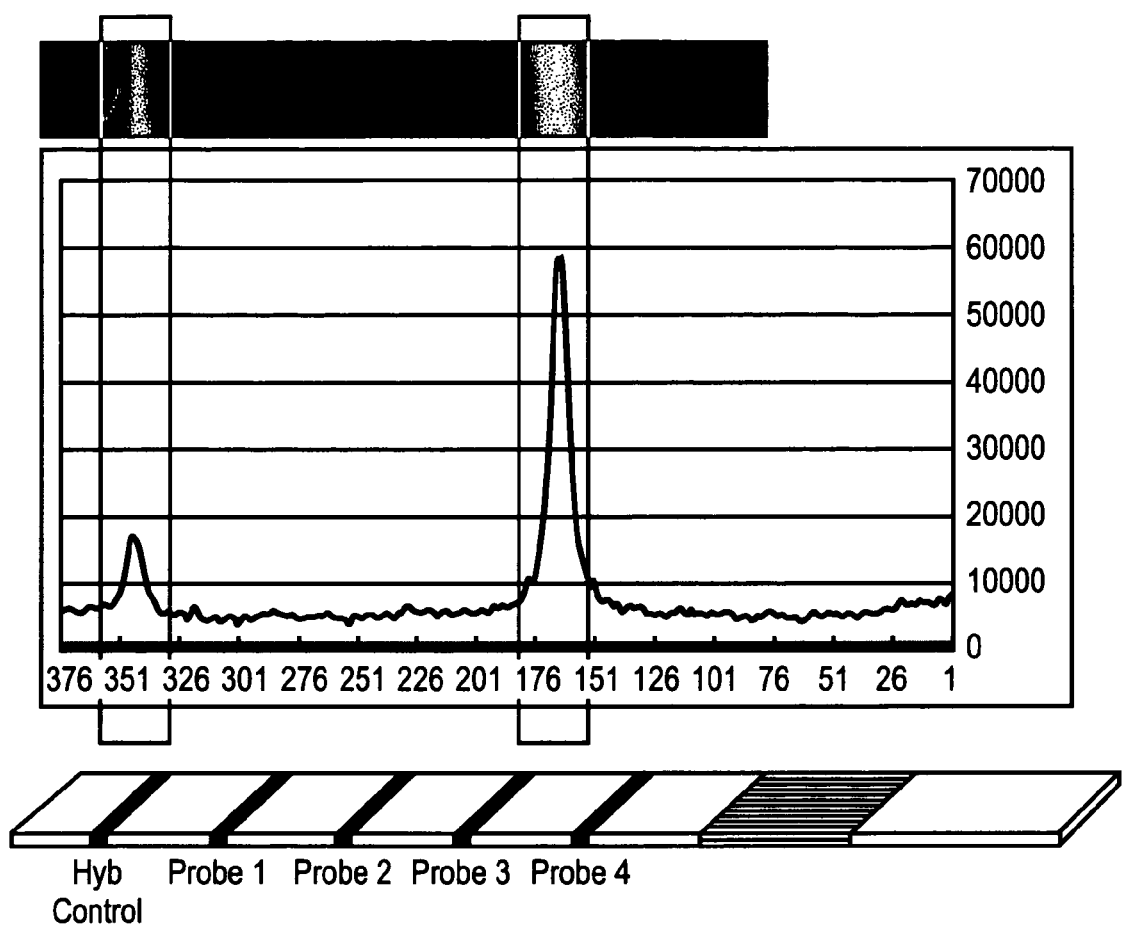
Figure 15:
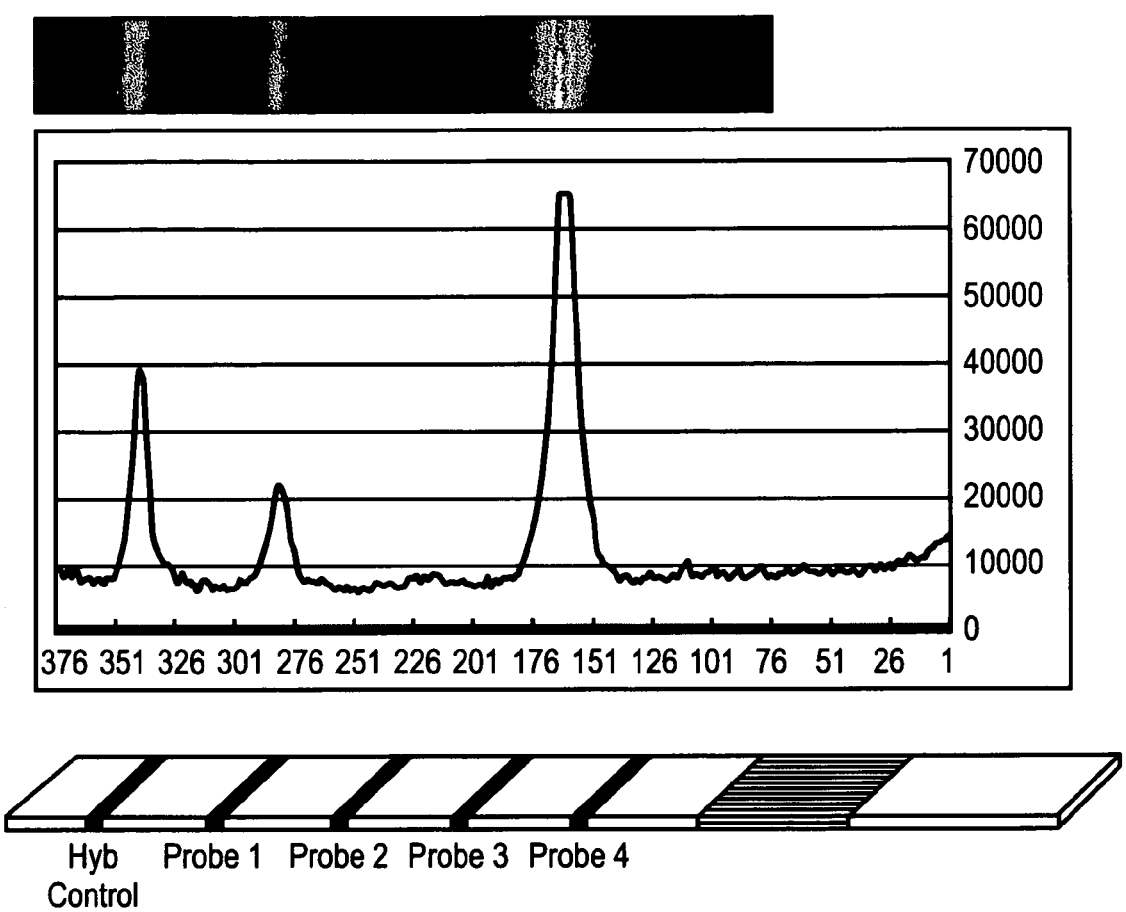
Figure 16:
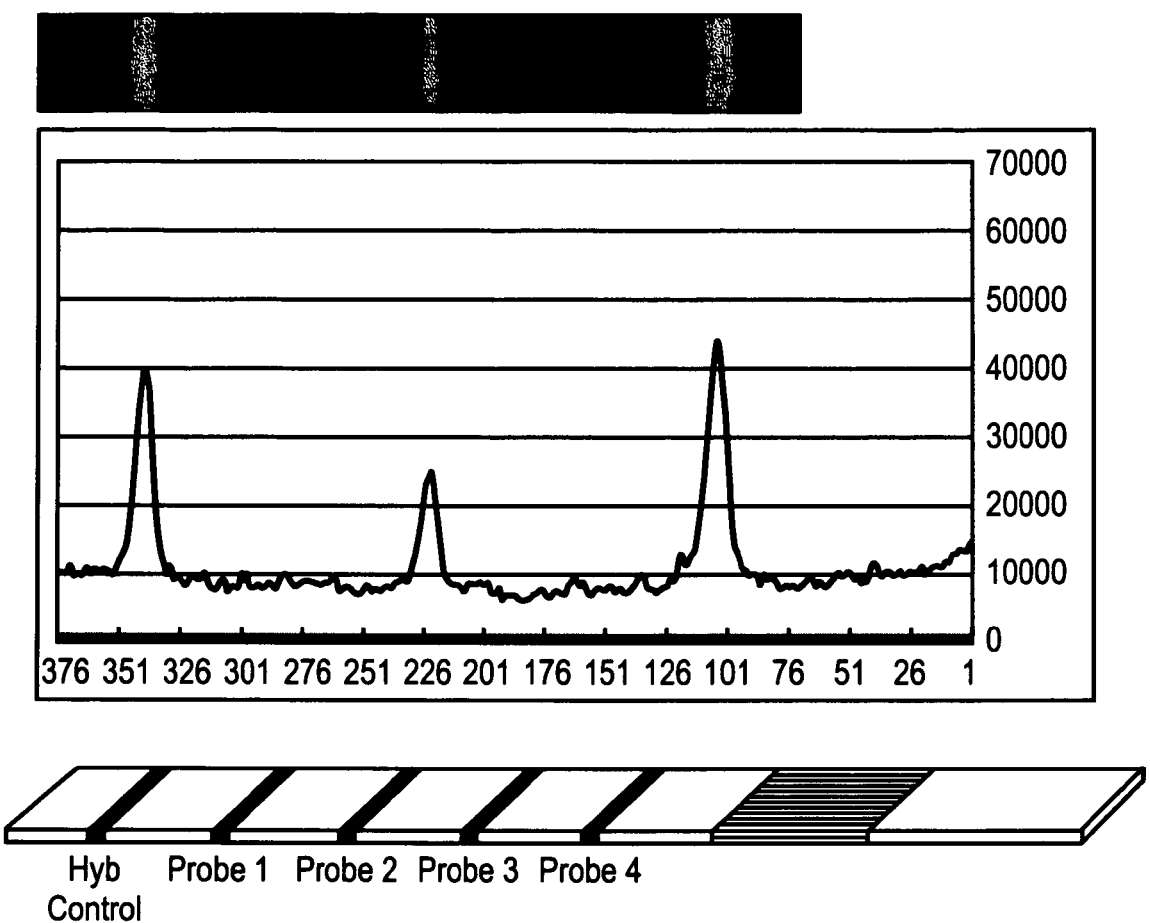

In order to apply a fluorescence-labeled primer or a PCR product and identify whether it is hybridized with the DNA immobilized on a glass fiber, the glass fiber substrate prepared above was assembled into a strip of the shape shown in FIG. 10. In order to carry out hybridization, 5 μℓ of fluorescence-labeled target DNA and 75 μℓ of BMT hyb-mixA were put into a 1.5 μℓ tube to prepare 80 μℓ of a mixed solution. Then, the thus-prepared solution was injected through the sample inlet of an assembled strip. Then, hybridization was carried out at a room temperature (20±5° C.) for 5~50 minutes. After hybridization has been completed, 100~300 μℓ of 0.1x~4x SSC solution was injected and then the strip was separated. Then, the glass fiber was attached to a slide, and then the fluorescence intensity was analyzed quantitatively by using a microarrayer scanner (GSI Lumonics, U.S.A.). FIG. 6 shows an illustrative embodiment of actual experiment results. The results show that fluorescence is visible only at the line having a desired base sequence, and that when letting genes flow over a glass fiber by using capillary action, microfluidics, or lateral flow, etc., a target DNA having a complementary base sequence can be specifically detected.

Example 6

Figure 7:
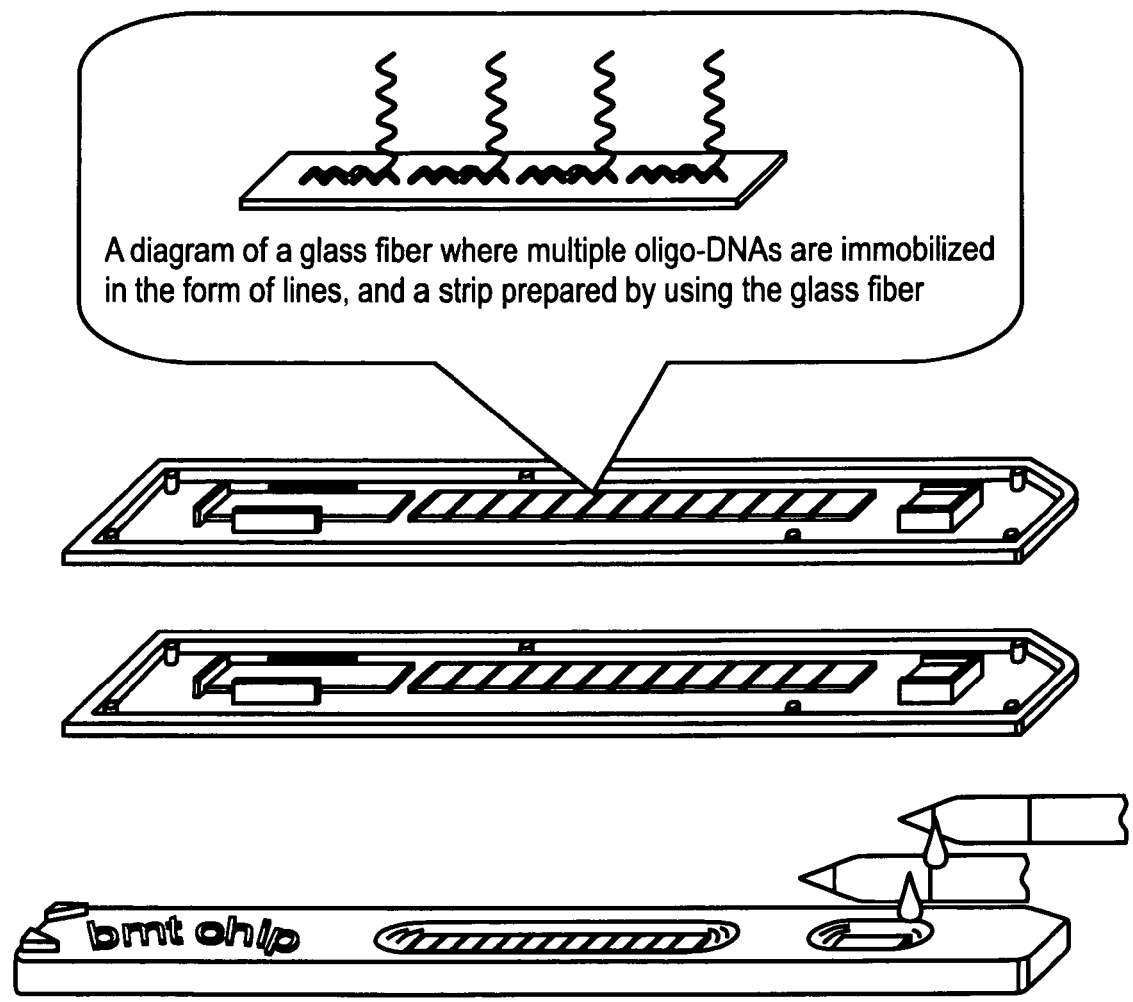
FIG. 7 is a diagram of an illustrative embodiment of a strip prepared by placing a glass fiber where multiple oligo-DNAs are immobilized into a strip and then covering it with a lid, according to one embodiment. When a solution including amplified genes obtained by PCR was injected through a sample inlet of the strip, gene hybridization results shown in FIGS. 5 and 6 were obtained. The results were analyzed mainly by spectrometry.
Figure 8:
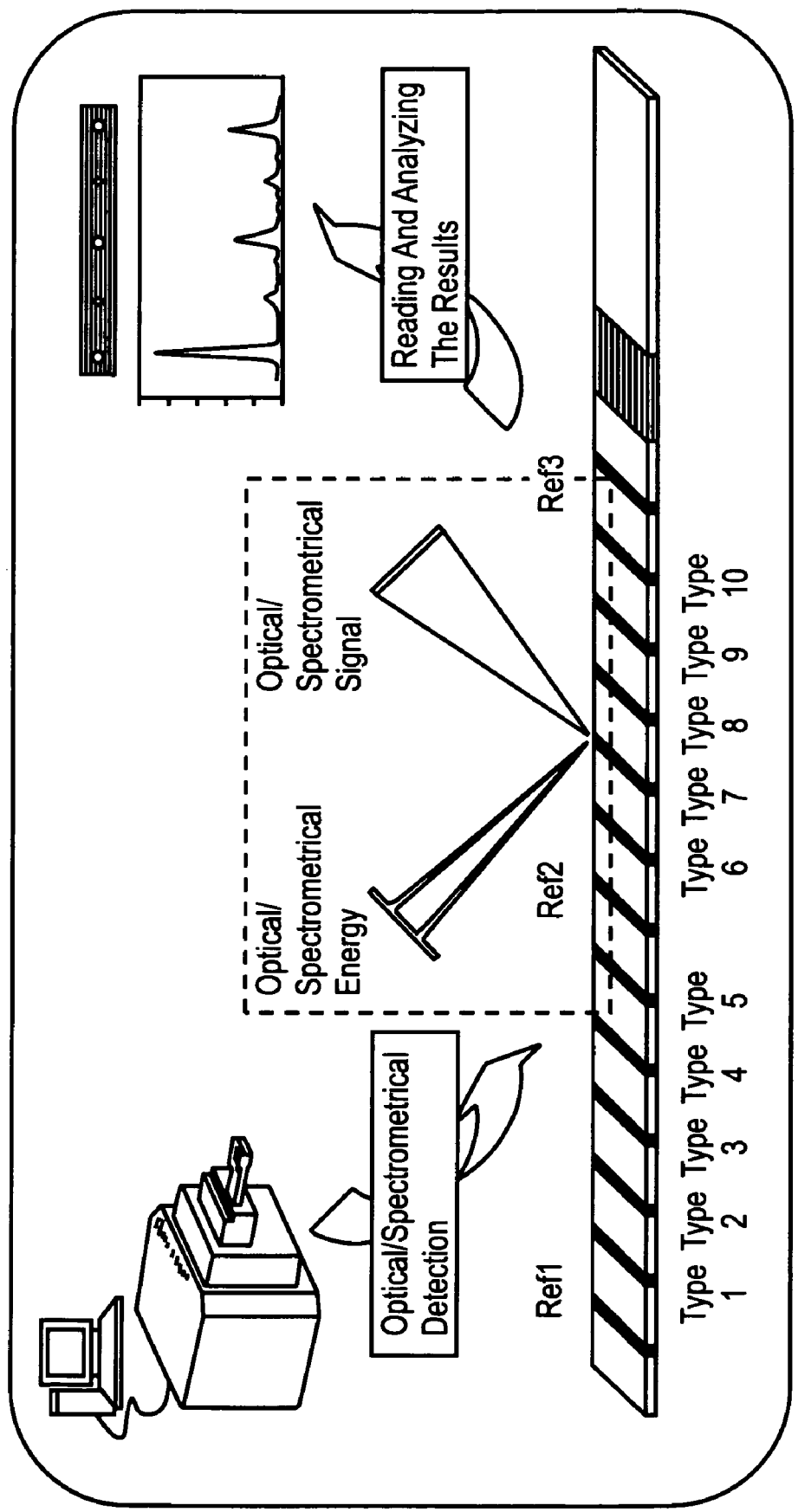
FIG. 8 is a diagram showing an illustrative embodiment of the method of analyzing the results by spectrometry after the process of FIG. 7 where the solution develops, according to one embodiment.

Experiment of Comparing with a Theoretical Maximum Amount of Genes that can be Immobilized on the Surface of a Glass Fiber In an illustrative embodiments, in order to carry out an experiment of comparing with a theoretical maximum amount of DNAs that can be immobilized on the surface of a glass fiber, probe DNA having consecutive guanine bases and a complementary base sequence was prepared and applied in the form of 5 lines on a modified glass fiber according to the same method as that of Example 3. In order to apply a fluorescence-labeled primer or a PCR product and identify whether it is hybridized with the DNA immobilized on a glass fiber, the glass fiber substrate prepared above was assembled into a strip of the shape shown in the diagram of FIG. 7 or the picture of FIG. 10. Hybridization was carried out according to the same method as that of Example 4. After hybridization has been completed, the glass fiber was detached from the strip. Then, the fluorescence intensity was analyzed quantitatively by using a microarrayer scanner (GSI Lumonics, U.S.A.) to obtain experimental data. In addition, in order to compare the experimental data with the theoretical maximum amount of genes that can be immobilized on the surface, a solution including a fluorescence-labeled gene in the concentration of 1× which is the same amount as the theoretical maximum amount of DNAs that can be immobilized on the surface was prepared. Then, said solution was diluted to ⅓, ⅑, ¹⁄₂₇, ¹⁄₈₁ folds. Then, each of the solutions was applied on a glass fiber in the form of a line by using a dispenser, and the glass fiber was dried. The results were read by using a fluorescence detector. FIG. 9 shows an illustrative embodiment of actual results.

Example 7

Method of Detecting the Lines Emerging on the Membrane of Said Modified Glass Fiber after Probe DNAs are Hybridized with Amplified Genes by Measuring Fluorescence A) Experiment of Identifying the Type of Gene by Using a Product Obtained by PCR by Using a Standard Material In an illustrative embodiment, standard materials used in this Example were purchased from ATCC (American Type Culture Collection), and are as follows:
Probe-1 (ATCC 45150)
Probe-2 (ATCC 45151)
Probe-3 (ATCC 45152)
Probe-4 (ATCC 45113)

While using plasmid DNA among the above as a template and the primers in Table 3, PCR was carried out according to the following method. The primers used in the PCR was synthesized by Bioneer Co. Ltd. (Republic of South Korea) by our order. PCR was carried out by treating a reaction solution purchased from Bionia Co. Ltd., including 10 µℓ of PCR buffer, 1 µℓ of 1.5 mM MgCl$_2$, 250 uM dNTP, 30 mM KCl, 10 mM Tris-HCl (pH9.0), Taq polymerase (1 unit) and primer (10 pmol/µℓ 7 µℓ of distilled water, and 1 µℓ of template DNA, at 94° C. for 5 minutes one time, and then 35 times repeating a treatment at 94° C. for 1 minute, at 45° C. for 45 seconds, and at 72° C. for 1 minute, and then treating the solution at 72° C. for 5 minutes one time. Then, 5 µℓ of the thus-prepared reaction solution was applied to 2% agarose gel along with a DNA size standard maker, and then it was subjected to electrophoresis. Here, the electrophoresis gel was dyed by 0.00005% ethidium bromide solution. Whether the band emerging on each of the paths in the gel is valid was confirmed by using UV.

TABLE 3

| Primer name | Base sequence (5'-3') |
|---|---|
| Forward | GATGGTGATATGGTAGATACAGGATTT |
| Cy5-Reverse* | Cy5-CCTAGTGGCTCTATGGTAACCTCTGACGC |

*Cy5 is a brand name of a compound having fluorescene activity, sold by Telechem Co. of U.S.A.

B) Method of Applying a Fluorescence-Labeled PCR Product and Hybridizing it with the Probe DNA Immobilized on a Glass Fiber and then Conducting an Analysis by Observing Fluorescence In an illustrative embodiment, in the Probe DNA immobilization shown in FIG. 4, a Biodot dispenser (Model No. XYZ 3050, U.S.A.) was used. 7-30 pmol/µℓ of probe DNAs having 9 consecutive guanine bases, including probe 1, probe 2, probe 3, probe 4, HC (Hybridization control) listed in Table 4, were dissolved in a BMT dispensing solution (100 mM ammonium ion solution) to prepare an immobilization solution. Said immobilization solution was dispensed at the rate of 20 mm/sec (0.7 ul/Cm) by using a dispensing nozzle, and was applied on a modified glass fiber manufactured by Biomatrix Technology Co. The probe DNAs were applied in the form of a linear band of 0.2-3.0 mm in thickness and immobilized spontaneously. The immobilization was carried out for 1~24 hours at the room temperature. Then, in order to block the locations where oligo-DNAs are not immobilized, the glass fiber was washed, and then immersed into 250 µℓ of BMT blocking solution (4×SSC; including 1% caseine and 0.5% Poly Ethylene Glycol) for 10~30 minutes, and then was dried in a 40-50° C. incubator for 30 minutes to 4 hours to prepare the strip shown in FIG. 10.

TABLE 4

| Probe name | Base sequence (5'-3') | Description |
|---|---|---|
| Probe-1 | GGG GGG GGG TCT GTA GCT ACT AGT ATT TAT GTA CAT ACA | Probe DNA |
| Probe-2 | GGG GGG GGG AGT ATA TAT GTT AAC ACC | Probe DNA |
| Probe-3 | GGG GGG GGG GT GTG TAT TCT CCC TCT | Probe DNA |
| Probe-4 | GGG GGG GGG T TCA AAT TAT TTT CCT ACA | Probe DNA |
| HC | GGG GGG GGG TTT ACA CCT AGT GGC TCT ATG GTG TCC TCT | Hybridization control |

C) Method of Applying a Fluorescence-Labeled PCR Product and Hybridizing it with Probe DNA Immobilized on a Glass Fiber and then Analyzing the Materials by Using Fluorescence In an illustrative embodiments, after hybridizing a fluorescence-labeled primer or PCR product with the DNA immobilized on a glass fiber, in order to identify whether a specific gene is bonded, the glass fiber or strip prepared by immobilizing probe DNAs on the glass fiber substrate prepared in Example 2 according to the method of Example 7-B) was assembled into a case of the shape shown in FIG. 10. Then, it was identified whether a specific gene is present by letting the PCR products develops over the glass fiber. In order to prepare a developing solution, 5 µℓ of PCR product prepared in Example 7-A) and 75 µℓ of BMT hyb-mix A were put into a 1.5 µℓ tube to prepare 80 µℓ of mixed solution. Then, the thus-prepared solution was heated in water at 100° C. for 3 minutes, and then cooled on ice for 3 minutes. Then, the 80 µℓ of mixed solution was injected through the sample inlet of an assembled strip. Then, the strip was left at the room temperature (20~30° C.) for 3-120 minutes so that the solution flows and hybridization can be carried out. Then, 100 µℓ of BMT Wa-B-2 (4×SSC) solution was injected, and after 5 minutes, the strip was separated. Then, the glass fiber (strip) was attached to a slide and then fluorescence intensity was analyzed quantitatively by using a microarrayer scanner (GSI Lumonics, U.S.A.). Actual results are shown in the strips at the top of FIG. 11 to FIG. 16. The graphs in the middle of FIG. 11 to FIG. 16 show illustrative embodiments of analysis results obtained by using BMT HPV strip reader type-1, which is used for analyzing a strip in BMT. As can be clearly seen from the drawings, in the case of the samples including the amplified genes complementary to probe DNAs, specific hybridization occurred at the bands (lines) where the complementary probe DNAs are immobilized, and hybridization was carried out in an HC area, too, making it possible to identify whether the samples were dispensed. Meanwhile, no hybridization occurred at the location of probe DNA of different type. That is, the drawings show that a strip-type chip capable of genotyping a gene amplified by PCR with high selectivity and low nonspecific hybridization rate has been developed and experimented.

The present application discloses world's first technology of modifying the surface of a glass fiber such that DNA can be immobilized on it, said technology including a surface-modified glass fiber whose surface is modified by an aminocalixarene derivative of formula 1 or an iminecalixarene derivative of formula 2 to form a monolayer, a method of preparing the same, a modified glass fiber where DNA is immobilized, a method of preparing the same, a method of preparing a genotyping strip using the glass fiber where DNA is immobilized, etc. The present disclosure remarkably improved existing technology by solving the cost problem resulting from the use of expensive scanner, providing convenience by removing complex processing, and achieving reproductibility by virtue of the uniform development of a solution.

In some embodiments, a glass fiber has a characteristic that a solution develops thereon at a specific speed, as in NC membrane used for a rapid kit. Accordingly, when oligo-DNA is immobilized on the surface of a glass fiber, gene included in a solution moving at a specific speed is hybridized at a constant speed while moving through the uniformly immobilized DNAs, thereby making it possible to prepare an article in the form of a strip which does not require a user's handling except when loading a sample. The present disclosure can remarkably increase the reproducibility of test results and increase convenience. In order to achieve the above effects, the present inventors have developed technology of modifying the surface of a glass fiber such that that DNA can be immobilized on it. Thus, the present disclosure achieved world's first technology of preparing a glass fiber where oligo-DNA is immobilized with a high density by improving conventional technology of modifying a glass slide. In addition, the present disclosure achieved technology of preparing a genotyping strip using the glass fiber where oligo-DNA is immobilized. Not only the strip prepared according to this technology can solve the problem occurring when preparing and using conventional oligo-DNA chips, such as that the test results are not reproducible and that the test results change depending on a user, but also can provide technology of preparing a DNA chip in the form of a glass slide-based strip, which allows genotyping using an inexpensive analyzer (i.e., without using an expensive analyzer costing tens of thousands of dollars). That is, the present disclosure is important in that it can solve the problem occurring when using conventional DNA chips, thereby allowing various diagnoses by using genotyping.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A glass fiber surface-modified by bonding an aminocalixarene derivative of formula 1 on a surface of an amine-modified glass fiber membrane to form a monolayer, wherein formula 1 comprises:

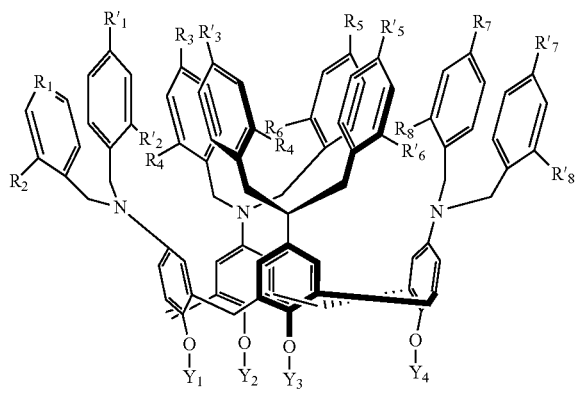

[formula 1]

wherein, $R_1, R_2, R_3, R_4, R_5, R_6, R_7, R_8, R'_1, R'_2, R'_3, R'_4, R'_5, R'_6, R'_7$ and $R'_8$ are independently selected from the group consisting of —H, —$CH_3$, —$C_2H_5$, —$C_3H_7$, —$OCH_3$, —Cl, —$C_6H_5$, —OH, —$OCH_2CH_3$, —Br, —$CF_3$, —$OCH_2C_6H_5$, —$OC_6H_5$, —$OC_6H_4CH_3$, —$OC_6H_4C(CH_3)_3$, —$OC_6H_4CF_3$, —$OC_6H_4Cl$, —$OCOCH_3$, —$NHCOCH_3$, —$CONHCH_3$, —CN, COOH, and —COOR wherein R represents —$CH_3$ or —$C_2H_5$;

$Y_1, Y_2, Y_3$ and $Y_4$ are independently selected from the group consisting of —H, —$(CH_2)_n$—CH=O, —$(CH_2)_n$—SH, —$(CH_2CH_2O)_m$—$CH_2CH_2$—CH=O, —$(CH_2CH_2O)_m$—$CH_2CH_2$—SH, —$(CH_2)_m$—$C_6H_4$—$(CH_2)_c$—Z and —CO—$(CH_2)_{m-1}$—$C_6H_4$—$(CH_2)_c$—Z, wherein, n=2~15, m=1~10, c=0~10, Z is a group selected from the group consisting of —SH, —CHO, —COOH and —$NH_2$, and —$C_6H_4$— and —$C_6H_5$ are defined as phenyl group.

2. A glass fiber surface-modified by bonding an iminecalixarene derivative of formula 2 on a surface of an amine-modified glass fiber membrane to form a monolayer, wherein formula 2 comprises:

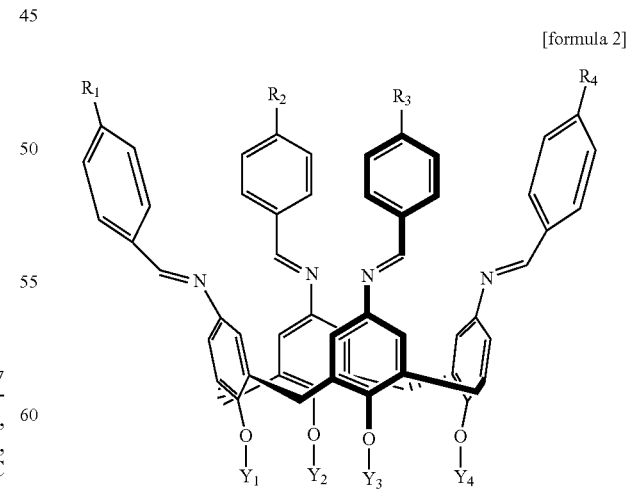

[formula 2]

wherein, $R_1, R_2, R_3$ and $R_4$ are independently selected from the group consisting of —H, —$CH_3$, —$C_2H_5$, —$C_3H_7$, —OCH$_3$, —Cl, —C$_6$H$_5$, —OH, —OCH$_2$CH$_3$, —Br, —CF$_3$, —OCH$_2$C$_6$H$_5$, —OC$_6$H$_5$, —OC$_6$H$_4$CH$_3$, —OC$_6$H$_4$C(CH$_3$)$_3$, —OC$_6$H$_4$CF$_3$, —OC$_6$H$_4$Cl, —OCOCH$_3$, —NHCOCH$_3$, —CONHCH$_3$, —CN, COOH, and —COOR wherein R represents —CH$_3$ or —C$_2$H$_5$;

Y$_1$, Y$_2$, Y$_3$ and Y$_4$ are independently selected from the group consisting of —H, —(CH$_2$)$_n$—CH=O, —(CH$_2$)$_n$—SH, —(CH$_2$CH$_2$O)$_m$—CH$_2$CH$_2$—CH=O, —(CH$_2$CH$_2$O)$_m$—CH$_2$CH$_2$—SH, —(CH$_2$)$_m$—C$_6$H$_4$—(CH$_2$)$_c$—Z and —CO—(CH$_2$)$_{m-1}$—C$_6$H$_4$—(CH$_2$)$_c$—Z, wherein, n=2~15, m=1~10, c=0~10, Z is a group selected from the group consisting of —SH, —CHO, —COOH and —NH$_2$, and —C$_6$H$_4$— and —C$_6$H$_5$ are defined as phenyl group.

3. A method for modifying a surface of a glass fiber membrane:
immersing a glass fiber membrane to which an amine functional group is attached, in a solution wherein a compound of formula 1 described in claim 1 is dissolved in an organic solvent;
washing the glass fiber membrane with the same solvent; and
drying the glass fiber membrane to form a monolayer of an aminocalixarene derivative.

4. A method for modifying a surface of a glass fiber membrane comprising:
immersing a glass fiber membrane to which an amine functional group is attached, in a solution wherein a compound of formula 2 described in claim 2 is dissolved in an organic solvent;
washing the glass fiber membrane with the same solvent; and
drying the glass fiber membrane to form a monolayer of an iminecalixarene derivative.

5. The glass fiber membrane according to claim 1, wherein an oligo-DNA having consecutive guanine bases is immobilized on a monolayer of an aminocalixarene derivative.

6. The glass fiber membrane according to claim 2, wherein an oligo-DNA having consecutive guanine bases is immobilized on a monolayer of an iminecalixarene derivative.

7. A method for preparing a glass fiber membrane comprising:
preparing an immobilization solution by dissolving an oligo-DNA having consecutive guanine bases in a dispensing solution;
dispensing the immobilization solution to the glass fiber membrane having a surface-modified with a monolayer of the aminocalixarene described in claim 1; and
immobilizing an oligo-DNA on the surface of the glass fiber membrane.

8. A method for preparing a glass fiber membrane comprising:
preparing a immobilization solution by dissolving an oligo-DNA having consecutive guanine bases in a dispensing solution;
dispensing the immobilization solution to the glass fiber membrane having a surface-modified with a monolayer of the iminecalixarene described in claim 2; and
immobilizing an oligo-DNA on the surface of the glass fiber membrane.

9. The glass fiber membrane according to claim 5, wherein the oligo-DNA is capable of identifying a gene having a specific base sequence by developing a solution containing fluorescence-labeled genes having an amplified nucleic acid.

10. The glass fiber membrane according to claim 6, wherein the oligo-DNA is capable of identifying a gene having a specific base sequence by developing a solution containing fluorescence-labeled genes having an amplified nucleic acid.

11. The glass fiber membrane according to claim 9, wherein the specific base sequence is a genotype of a virus.

12. The glass fiber membrane according to claim 10, wherein the specific base sequence is a genotype of a virus.

13. A strip for genotyping comprising the glass fiber membrane according to claim 5 containing at least one type of an oligo-DNA having consecutive guanine bases, wherein a sample inlet is formed on a part of the glass fiber membrane on which the oligo-DNA is not immobilized.

14. A strip for genotyping comprising the glass fiber membrane according to claim 6 containing at least one type of an oligo-DNA having consecutive guanine bases, wherein a sample inlet is formed on a part of the glass fiber on which the oligo-DNA is not immobilized.

15. A kit for genotyping, comprising the strip for genotyping according to claim 13 as a rapid strip type.

16. A kit for genotyping, comprising the strip for genotyping according to claim 14 as a rapid strip type.

17. The glass fiber membrane according to claim 1 wherein the glass fiber membrane is a woven membrane.

* * * * *

SEQUENCE LISTING

<160> NUMBER OF SEQ ID NOS: 10

<210> SEQ ID NO 1
<211> LENGTH: 28
<212> TYPE: DNA

```
<213> ORGANISM: Artificial Sequence
<220> FEATURE:
<223> OTHER INFORMATION: 9G DNA

<400> SEQUENCE: 1 gggggggga aatcaaccca cagctgca                                          28

<210> SEQ ID NO 2
<211> LENGTH: 19
<212> TYPE: DNA
<213> ORGANISM: Artificial Sequence
<220> FEATURE:
<223> OTHER INFORMATION: Cy-5 DNA

<400> SEQUENCE: 2
gtgcagctgt gggttgatt                                                   19

<210> SEQ ID NO 3
<211> LENGTH: 28
<212> TYPE: DNA
<213> ORGANISM: Artificial Sequence
<220> FEATURE:
<223> OTHER INFORMATION: M DNA

<400> SEQUENCE: 3 gggggggga gttcaaatta ttttccta                                          28

<210> SEQ ID NO 4
<211> LENGTH: 27
<212> TYPE: DNA
<213> ORGANISM: Artificial Sequence
<220> FEATURE:
<223> OTHER INFORMATION: Forward Primer

<400> SEQUENCE: 4
gatggtgata tggtagatac aggattt                                          27

<210> SEQ ID NO 5
<211> LENGTH: 29
<212> TYPE: DNA
<213> ORGANISM: Artificial Sequence
<220> FEATURE:
<223> OTHER INFORMATION: Cy-5 reverse primer

<400> SEQUENCE: 5
cctagtggct ctatggtaac ctctgacgc                                        29

<210> SEQ ID NO 6
<211> LENGTH: 39
<212> TYPE: DNA
<213> ORGANISM: Artificial Sequence
<220> FEATURE:
<223> OTHER INFORMATION: Probe-1

<400> SEQUENCE: 6 ggggggggt ctgtagctac tagtatttat gtacataca                              39

<210> SEQ ID NO 7
<211> LENGTH: 27
<212> TYPE: DNA
<213> ORGANISM: Artificial Sequence
<220> FEATURE:
<223> OTHER INFORMATION: Probe-2

<400> SEQUENCE: 7 gggggggga gtatatatgt taacacc                                           27
```

-continued

```
<210> SEQ ID NO 8
<211> LENGTH: 26
<212> TYPE: DNA
<213> ORGANISM: Artificial Sequence
<220> FEATURE:
<223> OTHER INFORMATION: Probe-3

<400> SEQUENCE: 8
gggggggggg tgtgtattct ccctct                                              26

<210> SEQ ID NO 9
<211> LENGTH: 28
<212> TYPE: DNA
<213> ORGANISM: Artificial Sequence
<220> FEATURE:
<223> OTHER INFORMATION: Probe-4

<400> SEQUENCE: 9 ggggggggt tcaaattatt ttcctaca                                             28

<210> SEQ ID NO 10
<211> LENGTH: 39
<212> TYPE: DNA
<213> ORGANISM: Artificial Sequence
<220> FEATURE:
<223> OTHER INFORMATION: Hybridization control

<400> SEQUENCE: 10 ggggggggt ttacacctag tggctctatg gtgtcctct                                 39
```